US012245840B2

(12) United States Patent
Dacosta et al.

(10) Patent No.: US 12,245,840 B2
(45) Date of Patent: Mar. 11, 2025

(54) MODULAR SYSTEM FOR MULTI-MODAL IMAGING AND ANALYSIS

(71) Applicant: MolecuLight Inc., Toronto (CA)

(72) Inventors: Ralph S. Dacosta, Etobicoke (CA); Simon Treadwell, Toronto (CA); Connor Wright, Toronto (CA); Kimberlyn Dampitan, Mississauga (CA); Todd Daynes, Aurora (CA); Todd Meaney, Thornhill (CA); Carl Annis, Oakville (CA); Danielle Dunham, Toronto (CA); Nitesh Mistry, Toronto (CA)

(73) Assignee: MolecuLight Inc., Toronto (CA)

( * ) Notice: Subject to any disclaimer, the term of this patent is extended or adjusted under 35 U.S.C. 154(b) by 633 days.

(21) Appl. No.: 17/423,447

(22) PCT Filed: Jan. 17, 2020

(86) PCT No.: PCT/IB2020/050385
§ 371 (c)(1),
(2) Date: Jul. 15, 2021

(87) PCT Pub. No.: WO2020/148726
PCT Pub. Date: Jul. 23, 2020

(65) Prior Publication Data
US 2022/0061671 A1    Mar. 3, 2022

Related U.S. Application Data

(60) Provisional application No. 62/793,842, filed on Jan. 17, 2019.

(51) Int. Cl.
*A61B 5/00*     (2006.01)
*A61B 46/17*    (2016.01)
*A61B 5/01*     (2006.01)

(52) U.S. Cl.
CPC .......... *A61B 5/0071* (2013.01); *A61B 5/0013* (2013.01); *A61B 5/0035* (2013.01);
(Continued)

(58) Field of Classification Search
CPC ... A61B 5/0071; A61B 5/0013; A61B 5/0035; A61B 5/0077; A61B 5/0086;
(Continued)

(56) References Cited

U.S. PATENT DOCUMENTS

| 3,945,371 A | 3/1976 | Adelman |
| D414,867 S | 10/1999 | Moriwaki et al. |

(Continued)

FOREIGN PATENT DOCUMENTS

| AU | 2014373656 | 7/2016 |
| CA | 208795 | 3/2022 |

(Continued)

OTHER PUBLICATIONS

Supplementary Partial European Search report dated Sep. 20, 2022 in related EP Application No. 20740856.8, 12 pages.
(Continued)

*Primary Examiner* — Rochelle D Turchen
(74) *Attorney, Agent, or Firm* — Jones Robb, PLLC; Elizabeth M. Burke; Dragan Plavsic

(57) ABSTRACT

A portable, modular handheld imaging system is disclosed. The modular system comprises a first housing portion and a second housing portion. The first housing portion includes at least one excitation light source. A first filter is configured to detect and permit passage of selected optical signals responsive to illumination with the excitation light to a first image sensor. A second filter is configured to detect and permit passage of selected optical signals responsive to illumination of the target surface with white light to a second image sensor. The second housing portion is configured to releas- (Continued)

ably receive the first housing portion. The second housing portion includes a display and a processor configured to receive the detected fluorescent and white light optical signals and to output a representation of the target surface to the display based on the detected optical signals.

79 Claims, 20 Drawing Sheets

(52) U.S. Cl.
CPC .......... *A61B 5/0077* (2013.01); *A61B 5/0086* (2013.01); *A61B 5/7445* (2013.01); *A61B 46/17* (2016.02); *A61B 5/01* (2013.01); *A61B 2560/0214* (2013.01); *A61B 2560/0233* (2013.01); *A61B 2560/0242* (2013.01); *A61B 2560/0443* (2013.01); *A61B 2562/0233* (2013.01)

(58) Field of Classification Search
CPC ......... A61B 5/7445; A61B 46/17; A61B 5/01; A61B 2560/0214; A61B 2560/0242; A61B 2560/0443; A61B 2562/0233
See application file for complete search history.

(56) References Cited

U.S. PATENT DOCUMENTS

| | | |
|---|---|---|
| 5,971,918 A | 10/1999 | Zanger |
| 6,190,309 B1 | 2/2001 | Ooshima et al. |
| 6,393,315 B1 | 5/2002 | Aprahamian et al. |
| 6,571,119 B2 | 5/2003 | Hayashi |
| 6,601,997 B2 | 8/2003 | Ngo |
| D480,478 S | 10/2003 | Leonard et al. |
| 6,678,398 B2 | 1/2004 | Wolters et al. |
| 6,889,075 B2 | 5/2005 | Marchitto et al. |
| D515,214 S | 2/2006 | Jackson, III et al. |
| D542,820 S | 5/2007 | Depay |
| D569,378 S | 5/2008 | Wanamaker |
| D585,554 S | 1/2009 | Suzuki |
| D605,759 S | 12/2009 | Cuevas et al. |
| D610,178 S | 2/2010 | Adolfsson et al. |
| 7,846,091 B2 | 12/2010 | Fulghum |
| D636,424 S | 4/2011 | Lin |
| D658,298 S | 4/2012 | Prpa |
| D677,793 S | 3/2013 | Prpa |
| 8,620,410 B2 | 12/2013 | Frangioni |
| D698,937 S | 2/2014 | Laverack et al. |
| D701,606 S | 3/2014 | Ohmukai |
| D703,331 S | 4/2014 | Kitayama |
| D703,333 S | 4/2014 | Saeki |
| D724,234 S | 3/2015 | Hagege |
| 9,042,967 B2 | 5/2015 | Dacosta et al. |
| D733,595 S | 7/2015 | Hoshino |
| D747,391 S | 1/2016 | Sakai |
| D748,808 S | 2/2016 | Matsumura et al. |
| D750,260 S | 2/2016 | Sauer |
| D753,308 S | 4/2016 | Marinkovich et al. |
| D755,062 S | 5/2016 | Yarden |
| 9,326,666 B2 | 5/2016 | Frangioni |
| 9,340,490 B2 | 5/2016 | Okura et al. |
| 9,451,882 B2 | 9/2016 | Nie et al. |
| D787,684 S | 5/2017 | Vezina |
| 9,743,836 B2 | 8/2017 | Tsubouchi et al. |
| D802,777 S | 11/2017 | Burachynsky et al. |
| D810,293 S | 2/2018 | Peel |
| D820,987 S | 6/2018 | Tam et al. |
| D822,747 S | 7/2018 | Van Deusen et al. |
| D822,748 S | 7/2018 | Van Deusen et al. |
| D827,014 S | 8/2018 | Sakai |
| D835,271 S | 12/2018 | Myers et al. |
| D849,105 S | 5/2019 | Hogstedt et al. |
| D850,628 S | 6/2019 | De Hoog et al. |
| D859,498 S | 9/2019 | Lin |
| D861,176 S | 9/2019 | Yoon et al. |
| D861,764 S | 10/2019 | Zhao |
| D862,697 S | 10/2019 | Kenworthy et al. |
| 10,438,356 B2 | 10/2019 | Dacosta |
| D865,836 S | 11/2019 | Puusaari |
| D865,845 S | 11/2019 | Sakai |
| D866,764 S | 11/2019 | Pukall |
| D868,867 S | 12/2019 | Jean et al. |
| D873,890 S | 1/2020 | Fidler |
| D884,175 S | 5/2020 | Aubailly et al. |
| D907,097 S | 1/2021 | Suurmeijer et al. |
| D908,161 S | 1/2021 | Dacosta et al. |
| D908,881 S | 1/2021 | Dacosta et al. |
| D921,736 S | 1/2021 | Yin |
| D910,105 S | 2/2021 | Lin |
| D910,182 S | 2/2021 | Dacosta et al. |
| D913,354 S | 3/2021 | Marzette, Jr. et al. |
| D914,220 S | 3/2021 | Nelson et al. |
| D916,294 S | 4/2021 | Murray et al. |
| D919,093 S | 5/2021 | Takahashi |
| D919,690 S | 5/2021 | Suurmeijer et al. |
| D921,899 S | 6/2021 | Suarez et al. |
| D922,469 S | 6/2021 | Sjogren et al. |
| D924,306 S | 7/2021 | Melnicoff |
| D930,845 S | 9/2021 | Schmidt et al. |
| D936,827 S | 11/2021 | Wang |
| D952,023 S | 5/2022 | Dacosta et al. |
| D958,991 S | 7/2022 | Dacosta et al. |
| D959,666 S | 8/2022 | Dacosta et al. |
| D967,420 S | 10/2022 | Sun |
| 2001/0049473 A1 | 12/2001 | Hayashi |
| 2003/0191368 A1 | 10/2003 | Wang et al. |
| 2004/0225222 A1 | 11/2004 | Zeng et al. |
| 2005/0029437 A1* | 2/2005 | Hasegawa .......... G02B 23/2407 250/226 |
| 2005/0234526 A1 | 10/2005 | Gilhuly et al. |
| 2005/0288594 A1 | 12/2005 | Lewkowicz et al. |
| 2006/0004292 A1 | 1/2006 | Beylin |
| 2006/0241493 A1 | 10/2006 | Feldman et al. |
| 2008/0059070 A1 | 3/2008 | Boyden et al. |
| 2008/0188758 A1 | 8/2008 | Campbell et al. |
| 2009/0137908 A1 | 5/2009 | Patwardhan |
| 2010/0084563 A1 | 4/2010 | Ohno |
| 2010/0145146 A1 | 6/2010 | Melder |
| 2010/0145419 A1 | 6/2010 | Fraval |
| 2010/0292580 A1 | 11/2010 | Gilhuly et al. |
| 2011/0117025 A1 | 5/2011 | Dacosta et al. |
| 2011/0275900 A1 | 11/2011 | Gilhuly et al. |
| 2011/0305422 A1 | 12/2011 | Thompson et al. |
| 2012/0016230 A1 | 1/2012 | Kishima et al. |
| 2012/0101390 A1 | 4/2012 | Iftimia et al. |
| 2012/0165627 A1 | 6/2012 | Yamamoto |
| 2012/0323124 A1 | 12/2012 | Corbett, III et al. |
| 2013/0338479 A1 | 12/2013 | Pogue et al. |
| 2014/0180116 A1 | 6/2014 | Lindekugel et al. |
| 2014/0275772 A1 | 9/2014 | Chuda |
| 2014/0276102 A1 | 9/2014 | Lee et al. |
| 2014/0276103 A1 | 9/2014 | Lee et al. |
| 2015/0030542 A1 | 1/2015 | Singhal |
| 2015/0038837 A1 | 2/2015 | Inoue et al. |
| 2015/0150460 A1 | 6/2015 | Krishnaswamy et al. |
| 2015/0182118 A1 | 7/2015 | Bradbury et al. |
| 2015/0182196 A1 | 7/2015 | Ninomiya et al. |
| 2015/0198797 A1* | 7/2015 | Andre .................. A61B 90/361 348/80 |
| 2015/0230696 A1* | 8/2015 | Tuch .................... A61B 5/0071 600/431 |
| 2016/0045114 A1 | 2/2016 | Dacosta et al. |
| 2016/0062103 A1 | 3/2016 | Yang et al. |
| 2016/0206202 A1 | 7/2016 | Frangioni |
| 2016/0287194 A1 | 10/2016 | Nariyuki et al. |
| 2016/0287211 A1 | 10/2016 | DaCosta et al. |
| 2017/0000320 A1 | 1/2017 | Wilson et al. |
| 2017/0085855 A1 | 3/2017 | Roberts et al. |
| 2017/0143418 A1 | 5/2017 | Lee |
| 2017/0156597 A1 | 6/2017 | Whitehead |
| 2017/0209050 A1 | 7/2017 | Fengler et al. |
| 2017/0235118 A1 | 8/2017 | Kuster et al. |

(56) References Cited

U.S. PATENT DOCUMENTS

| | | |
|---|---|---|
| 2017/0236281 A1* | 8/2017 | Dacosta .............. A61B 5/0077 382/128 |
| 2017/0280969 A1 | 10/2017 | Levy et al. |
| 2017/0290515 A1 | 10/2017 | Butte et al. |
| 2018/0014764 A1 | 1/2018 | Bechtel et al. |
| 2018/0070806 A1 | 3/2018 | Matsuo et al. |
| 2018/0098741 A1 | 4/2018 | Lu et al. |
| 2018/0133320 A1 | 5/2018 | Babic et al. |
| 2018/0218508 A1 | 8/2018 | Lee et al. |
| 2018/0234603 A1 | 8/2018 | Moore et al. |
| 2018/0242848 A1 | 8/2018 | Dacosta et al. |
| 2018/0252909 A1 | 9/2018 | Regensburger et al. |
| 2018/0276814 A1 | 9/2018 | Frangioni |
| 2018/0279864 A1 | 10/2018 | Frangioni |
| 2018/0310829 A1 | 11/2018 | Frangioni et al. |
| 2018/0325377 A1 | 11/2018 | Dacosta et al. |
| 2018/0369603 A1 | 12/2018 | Gjersvik et al. |
| 2019/0079011 A1 | 3/2019 | Frangioni |
| 2019/0159663 A1 | 5/2019 | Krstajic et al. |
| 2019/0209000 A1 | 7/2019 | Treado et al. |
| 2019/0216325 A1 | 7/2019 | Ouyang |
| 2020/0128166 A1 | 4/2020 | Fukumoto |
| 2020/0188033 A1 | 6/2020 | Komp et al. |
| 2020/0359884 A1 | 11/2020 | Swisher |
| 2021/0228300 A1 | 7/2021 | DaCosta et al. |
| 2021/0378584 A1 | 12/2021 | Takahashi et al. |
| 2022/0007942 A1 | 1/2022 | Stith et al. |
| 2022/0061671 A1 | 3/2022 | Dacosta et al. |
| 2022/0071559 A1 | 3/2022 | Jones et al. |
| 2022/0072294 A1 | 3/2022 | Locke et al. |
| 2022/0248944 A1 | 8/2022 | DaCosta et al. |

FOREIGN PATENT DOCUMENTS

| | | |
|---|---|---|
| CN | 101208037 | 6/2008 |
| CN | 103654699 | 3/2014 |
| CN | 104271046 | 1/2015 |
| CN | 104394754 | 3/2015 |
| CN | 106714670 | 5/2017 |
| CN | 106983495 | 7/2017 |
| CN | 107093171 | 8/2017 |
| CN | 304554755 | 3/2018 |
| CN | 108289723 | 7/2018 |
| CN | 306141139 | 10/2020 |
| CN | 307182522 | 9/2022 |
| CN | 307545922 | 9/2022 |
| CN | 307713119 | 12/2022 |
| EM | 006624763-0002 | 7/2019 |
| EP | 1880660 | 1/2008 |
| EP | 2502551 | 9/2012 |
| EP | 3372143 | 9/2018 |
| EP | 4284131 | 11/2023 |
| JP | H09-000488 | 1/1997 |
| JP | 2004305367 | 11/2004 |
| JP | 2007244746 | 9/2007 |
| JP | 2011521237 | 7/2011 |
| JP | 2012532689 | 12/2012 |
| JP | 2013514156 | 4/2013 |
| JP | 2013531538 | 8/2013 |
| JP | 2015139613 | 8/2015 |
| JP | 2016030214 | 3/2016 |
| JP | 2016-520339 | 7/2016 |
| JP | 2017060778 | 3/2017 |
| JP | 2017524935 | 8/2017 |
| JP | 2017192501 | 10/2017 |
| KR | 300827516.0000 | 11/2015 |
| WO | 2010080611 | 7/2010 |
| WO | 2013184830 | 12/2013 |
| WO | 2016011534 | 1/2016 |
| WO | 2016063949 | 4/2016 |
| WO | 2017079844 | 5/2017 |
| WO | 2017082242 | 5/2017 |
| WO | 2017096137 | 6/2017 |
| WO | 2018145193 | 8/2018 |
| WO | 2019148268 | 8/2019 |
| WO | 2019213737 | 11/2019 |
| WO | 2020148724 | 7/2020 |
| WO | 2020148725 | 7/2020 |
| WO | 2020148726 | 7/2020 |

OTHER PUBLICATIONS

Supplementary European Search report dated Sep. 20, 2022 in related EP Application No. 20741034.1, 27 pages.
Supplementary European Search report dated Sep. 26, 2022 in related EP Application No. 20741678.5, 9 pages.
Office Action dated Sep. 16, 2022 in related CA Application No. 3,127,036.
Notice of Allowance dated Sep. 27, 2022 in related JP Application No. 2022-003401.
Office Action dated Oct. 6, 2022 in related CA Application No. 3,127,048.
Office Action dated Sep. 27, 2022 in related JP Application No. 2022-019073.
Notice of Allowance in Design U.S. Appl. No. 29/762,417, dated Jan. 13, 2022, 13 pages.
Notice of Allowance in Design U.S. Appl. No. 29/767,502 dated Mar. 11, 2022, 5 pages.
Notice of Allowance in U.S. Appl. No. 29/767,874 dated Mar. 21, 2022.
Examination Report dated Mar. 24, 2022 in IN App No. 358348-001.
Examination Report dated Mar. 24, 2022 in IN App No. 358347-001.
Office Action dated Apr. 4, 2023 received in related JP Application No. 2020-541946.
Written Opinion dated Apr. 21, 2023 in related Application No. 11202107275Q.
First Examination report dated Jun. 30, 2022 in related IN App No. 202017037681.
European Search report dated Jan. 5, 2023 in related EP Application No. 20740856. 8.
First Examination report dated Feb. 3, 2023 in related IN App No. 202117030136.
Examination Report dated Feb. 16, 2022 in CA App No. 204823.
First Examination report dated Apr. 29, 2022 in IN App No. 358346-001.
U.S. Appl. No. 62/793,842, dated Jan. 17, 2019.
U.S. Appl. No. 62/793,846, dated Jan. 17, 2019.
U.S. Appl. No. 62/857,183, dated Jun. 4, 2019.
Design U.S. Appl. No. 29/676,901, dated Jan. 15, 2019.
International Search Report and Written Opinion from International Patent Application No. PCT/CA2019/000015, dated Jun. 4, 2019.
"Fluorescent chemical probes for accurate tumor diagnosis and targeting therapy", 2017, Gao et al. https://www.researchgate.net/publication/315469453 Fluorescent chemical probes for accurate tumor diagnosis and targeting therapy.
"Current concepts and future perspectives on surgical optical imaging in cancer",2010, Ntziachristos et al., https://www.sniedigitallibrary.orMoumals/Jounial-of-Biomedical-Onticstvolume-15issue-61066024/Current-concepts-and-future-perspectives-on-surgical-optical-imaging-in/10.1117/1.3523364.full7SSO=I.
Notice of Allowance in Design U.S. Appl. No. 29/677,154, dated Apr. 1, 2020.
Notice of Allowance in Design U.S. Appl. No. 29/677,152, dated Apr. 1, 2020.
Ex Parte Quayle Action in Design U.S. Appl. No. 29/676,901, dated Mar. 5, 2020.
Notice of Allowance in Design U.S. Appl. No. 29/676,901, dated Jun. 4, 2020.
Notice of Allowance in Design U.S. Appl. No. 29/677,152, dated Sep. 22, 2020.
Notice of Allowance in Design U.S. Appl. No. 29/676,901, dated Sep. 18, 2020.
Ex Parte Quayle Action in Design U.S. Appl. No. 29/677,152, dated Dec. 20, 2019.

(56) References Cited

OTHER PUBLICATIONS

Design U.S. Appl. No. 29/762,417, dated Dec. 16, 2020.
Design U.S. Appl. No. 29/767,502, dated Jan. 22, 2021.
U.S. Appl. No. 17/423,576, dated Jul. 16, 2021.
U.S. Appl. No. 17/423,609, dated Jul. 16, 2021.
Office Action dated Aug. 17, 2021 in related U.S. Appl. No. 29/762,417, 9 pages.
Design U.S. Appl. No. 29/804,808, dated Aug. 23, 2021.
European Search Report for EP Application No. EP19746801 dated Sep. 13, 2021, 2 pages.
"Nagaya et al" Fluorescence-Guided Surgery, Frontiers in Oncology, vol. 7, Dec. 22, 2017, 16 pp.
Design U.S. Appl. No. 29/677,152, dated Jan. 17, 2019.
International Search Report and Written Opinion from International Application No. PCT/IB2020/050385, dated Apr. 8, 2020.
International Search Report and Written Opinion from International Application No. PCT/IB2020/050384, dated Apr. 22, 2020.
International Search Report and Written Opinion from International Application No. PCT/IB2020/050383, dated Apr. 23, 2020.
U.S. Appl. No. 29/842,182, filed Jun. 10, 2022.
U.S. Appl. No. 29/842,512, filed Jun. 14, 2022.
Office Action dated Jun. 21, 2022 in related Brazilian Application No. BR 302022000890-7.
Office Action dated Jul. 13, 2023 in related CA Application No. 3,127,048.
Decision of Rejection dated Jul. 25, 2023 in related JP Application No. 2020-541946.
Office Action dated Jul. 14, 2023 in related CA Application No. 3,127,036.
Notification of the First Rectification dated Jul. 5, 2023 in related CN Application No. 2022300861326.
Office Action dated Jun. 20, 2023 received in related JP Application No. 2023-003578.
Examination Report dated Aug. 10, 2023 in related CA Application No. 210515.
Office Action dated Oct. 3, 2023 received in related U.S. Appl. No. 29/842,512, 8 pages.
Baycare, Lumicell, Inc. Selects BayCare for Pivotal Breast Cancer Trial, Published on: Oct. 9, 2020, Baycare.org, Retrieved from Internet: https://baycare.org/newsroom/2020/october/lumicell-inc-selects-baycare-for-pivotal-breast-cancer-clinical-trial (Year: 2020).
Office Action dated Oct. 3, 2023 received in related JP Application No. 2021-541493.
Office Action dated Oct. 3, 2023 received in related JP Application No. 2021-541474.
Notice of Allowance dated Oct. 13, 2023 in related U.S. Appl. No. 29/842,182, 9 pages.
Advanced Endoscopy Devices, Inc, Introducing the Multi-Disciplinary Use of the AED ENDOPRO-CAM® Elite, Uploaded on: Mar. 11, 2020, YouTube, Retrieved from Internet: https://www.youtube.com/watch?v=rnxtMz2JhFg (Year: 2020).
SBI ALAPharma, The Eagle V1.2 Imaging System, Downloaded on: Aug. 22, 2023, sbi-alapharmacanada.ca, Retrieved from Internet: https://www.sbi-alapharmacanada.ca/technology (Year: 2023).
Office Action dated Nov. 7, 2023 received in related JP Application No. 2021-541486.
Office Action dated Sep. 27, 2023 received in related CN Application No. 2020800191924.
Office Action dated Nov. 4, 2023 received in related CA Application No. 225,390.
Office Action dated Sep. 28, 2023 received in CN Application No. 2019800233835.
Examination report dated Nov. 30, 2023 received in AU Application No. 2019215811.
European Search Report dated Jan. 12, 2024 received in EP Application No. 23188747.2.
Office Action dated Jan. 17, 2024 in related CN Application No. 2020800184047.
Office Action dated Jan. 24, 2024 in related U.S. Appl. No. 16/966,293, 18 pp.
Office Action dated Oct. 12, 2023 in related CN Application No. 2020800219686.
Office Action dated Jan. 11, 2024 in related CN Application No. 2022300861326.
Notice of Allowance dated Feb. 5, 2024 in related U.S. Appl. No. 29/842,512.
Office Action dated Feb. 22, 2024 in related U.S. Appl. No. 17/423,576, 26 pp.
Office Action dated Jan. 26, 2024 in related MX Application No. MX/f/2022/000423.
Office Action dated Mar. 27, 2024 in related CA Application No. 3,127,039.
Office Action dated Mar. 28, 2024 in related CA Application No. 3,090,190.
Office Action dated Apr. 3, 2024 in related CN Application No. 2019800233835.
Office Action dated Jun. 28, 2024 received in related CN Application No. 2019800233835.
Office Action dated Jul. 4, 2024 received in related CN Application No. 2020800191924.
Office Action dated Sep. 2, 2024 received in related EP Application No. 19746801.0.
Office Action dated Sep. 3, 2024 received in related JP Application No. 2023-199730.
Office Action dated May 23, 2024 in related MX Application No. MX/f/2022/000423.
Notice of Grant dated Jun. 11, 2024 Issued in related JP Application No. 2021-541486.
Notice of Allowance dated May 27, 2024 in related MX/f/2024/000967.
Notice of Allowance dated May 27, 2024 in related MX/f/2024/000968.
Office Action dated Jul. 16, 2024 received in related JP Application No. 2021-541493.
Office Action dated Jul. 16, 2024 received in related JP Application No. 2021-541474.
Notice of Allowance dated Jun. 11, 2024 in related CA Application No. 3,127,048.
Office Action dated Jul. 25, 2024 in related MX Application No. MX/a/2021/008504.
Examination Report dated Sep. 6, 2024 received in related AU Application No. 2020209518.
Examination Report dated Sep. 5, 2024 received in related AU Application No. 2020209276.
Office Action dated Aug. 6, 2024 received in related CN Application No. 2020800219686.
Examination Report dated Sep. 27, 2024 received in related AU Application No. 2020208843.
Office Action dated Oct. 16, 2024 received in related CN Application No. 2019800233835.
Office Action dated Nov. 14, 2024 received in related Korean Application No. 10-2021-7026033.
Office Action dated Sep. 26, 2024 in related U.S. Appl. No. 17/423,609, 52 pp.
Final Office Action dated Nov. 1, 2024 received in related U.S. Appl. No. 17/423,576, 22 pages.
Final Office Action dated Nov. 7, 2024 received in related U.S. Appl. No. 16/966,293, 21 pp.
Office Action dated Oct. 17, 2024 received in related CN Application No. 2020800184047.
Office Action dated Oct. 24, 2024 in related Canadian Application No. 3,127,036.

* cited by examiner

MODULAR SYSTEM FOR MULTI-MODAL IMAGING AND ANALYSIS

CROSS REFERENCE FOR RELATED APPLICATIONS

This application is a U.S. national stage application under 35 U.S.C. § 371 (c) of International Application No. PCT/IB2020/050385, filed Jan. 17, 2020, which claims priority to Provisional Application No. 62/793,842, entitled "MODULAR SYSTEM FOR MULTI-MODAL IMAGING AND ANALYSIS," filed on Jan. 17, 2019, the entire content of which are each incorporated by reference herein.

TECHNICAL FIELD

A system for multi-modal imaging and analysis is disclosed. In particular, the system and method may be suitable for collecting data regarding biochemical, biological and/or non-biological substances. The data may include, for example, one or more of white light data, fluorescent data, thermal data, infrared data, such as in wound care for both human and animal applications.

BACKGROUND

Wound care is a major clinical challenge. Healing and chronic non-healing wounds are associated with a number of biological tissue changes including inflammation, proliferation, remodeling of connective tissues and, a common major concern, bacterial infection. A proportion of wound infections are not clinically apparent and contribute to the growing economic burden associated with wound care, especially in aging populations. Currently, the gold-standard wound assessment includes direct visual inspection of the wound site under white light combined with indiscriminate collection of bacterial swabs and tissue biopsies resulting in delayed, costly and often insensitive bacteriological results. This may affect the timing and effectiveness of treatment. Qualitative and subjective visual assessment only provides a gross view of the wound site, but does not provide information about underlying biological and molecular changes that are occurring at the tissue and cellular level. A relatively simple and complementary method that exploits 'biological and molecular' information to improve the early identification of such occult change is desirable in clinical wound management. Early recognition of high-risk wounds may guide therapeutic intervention and provide response monitoring over time, thus greatly reducing both morbidity and mortality due especially to chronic wounds.

Wound care and management is major clinical challenge that presents a significant burden and challenge to health care globally [Bowler et al., Clin Microbiol Rev. 2001, 14:244-269; Cutting et al., Journal of Wound Care. 1994, 3:198-201; Dow et al., Ostomy/Wound Management. 1999, 45:23-40]. Wounds are generally classified as, wounds without tissue loss (e.g. in surgery), and wounds with tissue loss, such as burn wounds, wounds caused as a result of trauma, abrasions or as secondary events in chronic ailments (e.g., venous stasis, diabetic ulcers or pressure sores and iatrogenic wounds such as skin graft donor sites and dermabrasions, pilonidal sinuses, non-healing surgical wounds and chronic cavity wounds). Wounds are also classified by the layers involved, superficial wounds involve only the epidermis, partial thickness wounds involve only epidermis and dermis, and full thickness wounds involve the subcutaneous fat or deeper tissue as well as epidermis and dermis.

Although restoration of tissue continuity after injury is a natural phenomenon, infection, quality of healing, speed of healing, fluid loss and other complications that enhance the healing time represents a major clinical challenge. The majority of wounds heal without any complication. However, chronic non-healing wounds involving progressively more tissue loss result in a large challenge for wound-care practitioners and researchers. Unlike surgical incisions where there is relatively little tissue loss and wounds generally heal without significant complications, chronic wounds disrupt the normal process of healing which is often not sufficient in itself to effect repair. Delayed healing is generally a result of compromised wound physiology [Winter (1962) Nature. 193:293-294] and typically occurs with venous stasis and diabetic ulcers, or prolonged local pressure as in immuno-suppressed and immobilized elderly individuals. These chronic conditions increase the cost of care and reduce the patient's quality of life. As these groups are growing in number, the need for advanced wound care products will increase.

Conventional clinical assessment methods of acute and chronic wounds continue to be suboptimal. They are usually based on a complete patient history, qualitative and subjective clinical assessment with simple visual appraisal using ambient white light and the 'naked eye', and can sometimes involve the use of color photography to capture the general appearance of a wound under white light illumination [Perednia (1991) J Am Acad Dermatol. 25: 89-108]. Regular re-assessment of progress toward healing and appropriate modification of the intervention is also necessary. Wound assessment terminology is non-uniform, many questions surrounding wound assessment remain unanswered, agreement has yet to be reached on the key wound parameters to measure in clinical practice, and the accuracy and reliability of available wound assessment techniques vary. Visual assessment is frequently combined with swabbing and/or tissue biopsies for bacteriological culture for diagnosis. Bacterial swabs are collected at the time of wound examination and have the noted advantage of providing identification of specific bacterial/microbial species [Bowler, 2001; Cutting, 1994; Dow, 1999; Dow G. In: Krasner et al. eds. Chronic Wound Care: A Clinical Source Book for Healthcare Professionals, 3rd ed. Wayne Pa.: HMP Communications. 2001:343-356]. However, often, multiple swabs and/or biopsies are collected randomly from the wound site, and some swabbing techniques may in fact spread the microorganisms around with the wound during the collection process thus affecting patient healing time and morbidity [Dow, 1999]. This may be a problem especially with large chronic (non-healing) wounds where the detection yield for bacterial presence using current swabbing and biopsy protocols is suboptimal (diagnostically insensitive), despite many swabs being collected. Thus, current methods for obtaining swabs or tissue biopsies from the wound site for subsequent bacteriological culture are based on a non-targeted or 'blind' swabbing or punch biopsy approach and have not been optimized to minimize trauma to the wound or to maximize the diagnostic yield of the bacteriology tests. In addition, obtaining swabs and biopsy samples for bacteriology can be laborious, invasive, painful, costly, and more importantly, bacteriological culture results often take about 2-3 days to come back from the laboratory and can be inconclusive [Serena et al. (2008) Int J Low Extrem Wounds. 7(1):32-5.; Gardner et al., (2007) WOUNDS. 19(2):31-38], thus delaying accurate diagnosis and treatment [Dow, 1999]. Thus, bacterial swabs do not provide real-time detection of infectious status of wounds. Although wound swabbing appears to be straightforward, it can lead to inappropriate treatment, patient morbidity and increased hospital stays if not performed correctly [Bowler, 2001; Cutting, 1994; Dow, 1999; Dow, 2001]. The lack of a non-invasive imaging method to objectively and rapidly evaluate wound repair at a biological level (which may be at greater detail than simply appearance or morphology based), and to aid in targeting of the collection of swab and tissue biopsy samples for bacteriology is a major obstacle in clinical wound assessment and treatment. An alternative method is highly desirable.

As wounds (chronic and acute) heal, a number of key biological changes occur at the wound site at the tissue and cellular level [Cutting, 1994]. Wound healing involves a complex and dynamic interaction of biological processes divided into four overlapping phases—hemostasis, inflammation, cellular proliferation, and maturation or remodeling of connective tissues—which affect the pathophysiology of wound healing [Physiological basis of wound healing, in Developments in wound care, PJB Publications Ltd., 5-17, 1994]. A common major complication arising during the wound healing process, which can range from days to months, is infection caused by bacteria and other microorganisms [Cutting, 1994; Dow, 1999]. This can result in a serious impediment to the healing process and lead to significant complications. All wounds contain bacteria at levels ranging from contamination, through colonization, critical colonization to infection, and diagnosis of bacterial infection is based on clinical symptoms and signs (e.g., visual and odorous cues).

The most commonly used terms for wound infection have included wound contamination, wound colonisation, wound infection and, more recently, critical colonisation. Wound contamination refers to the presence of bacteria within a wound without any host reaction [Ayton M. Nurs Times 1985, 81(46): suppl 16-19], wound colonisation refers to the presence of bacteria within the wound which do multiply or initiate a host reaction [Ayton, 1985], Critical colonisation refers to multiplication of bacteria causing a delay in wound healing, usually associated with an exacerbation of pain not previously reported but still with no overt host reaction [Falanga et al., J Invest Dermatol 1994, 102(1): 125-27; Kingsley A, Nurs Stand 2001, 15(30): 50-54, 56, 58]. Wound infection refers to the deposition and multiplication of bacteria in tissue with an associated host reaction [Ayton, 1985]. In practice the term 'critical colonisation' can be used to describe wounds that are considered to be moving from colonisation to local infection. The challenge within the clinical setting, however, is to ensure that this situation is quickly recognized with confidence and for the bacterial bioburden to be reduced as soon as possible, perhaps through the use of topical antimicrobials. Potential wound pathogens can be categorised into different groups, such as, bacteria, fungi, spores, protozoa and viruses depending on their structure and metabolic capabilities [Cooper et al., Wound Infection and Microbiology.: Medical Communications (UK) Ltd for Johnson & Johnson Medical, 2003]. Although viruses do not generally cause wound infections, bacteria can infect skin lesions formed during the course of certain viral diseases. Such infections can occur in several settings including in health-care settings (hospitals, clinics) and at home or chronic care facilities. The control of wound infections is increasingly complicated, yet treatment is not always guided by microbiological diagnosis. The diversity of micro-organisms and the high incidence of polymicrobic flora in most chronic and acute wounds gives credence to the value of identifying one or more bacterial pathogens from wound cultures. The early recognition of causative agents of wound infections can assist wound care practitioners in taking appropriate measures. Furthermore, faulty collagen formation arises from increased bacterial burden and results in over-vascularized friable loose granulation tissue that usually leads to wound breakdown [Sapico et al. (1986) Diagn Microbiol Infect Dis. 5:31-38].

Accurate and clinically relevant wound assessment is an important clinical tool, but this process currently remains a substantial challenge. Current visual assessment in clinical practice only provides a gross view of the wound site (e.g., presence of purulent material and crusting). Current best clinical practice fails to adequately use the critically important objective information about underlying key biological changes that are occurring at the tissue and cellular level (e.g., contamination, colonization, infection, matrix remodeling, inflammation, bacterial/microbial infection, and necrosis) since such indices are i) not easily available at the time of the wound examination and ii) they are not currently integrated into the conventional wound management process. Direct visual assessment of wound health status using white light relies on detection of color and topographical/textural changes in and around the wound, and thus may be incapable and unreliable in detecting subtle changes in tissue remodeling. More importantly, direct visual assessment of wounds often fails to detect the presence of bacterial infection, since bacteria are occult under white light illumination. Infection is diagnosed clinically with microbiological tests used to identify organisms and their antibiotic susceptibility. Although the physical indications of bacterial infection can be readily observed in most wounds using white light (e.g., purulent exudate, crusting, swelling, erythema), this is often significantly delayed, and the patient is already at increased risk of morbidity (and other complications associated with infection) and mortality. Therefore, standard white light direct visualization fails to detect the early presence of the bacteria themselves or identify the types of bacteria within the wound.

Implantation and grafting of stem cells have recently become of interest, such as for wound care and treatment. However, it is currently challenging to track the proliferation of stem cells after implantation or grafting. Tracking and identifying cancer cells have also been challenging. It would be desirable if such cells could be monitored in a minimally-invasive or non-invasive way.

It is also useful to provide a way for detecting contamination of other target surfaces, including non-biological targets.

SUMMARY

The present disclosure may solve one or more of the above-mentioned problems and/or may demonstrate one or more of the above-mentioned desirable features. Other features and/or advantages may become apparent from the description that follows.

In accordance with one aspect of the present disclosure, a portable, handheld imaging system is provided. The system comprises at least one excitation light source configured to emit excitation light during fluorescent imaging. A first filter is configured to detect and permit passage of optical signals, responsive to illumination of a target surface with the excitation light and having a wavelength corresponding to one or more of bacterial fluorescence, bacterial autofluorescence, tissue fluorescence, and tissue autofluorescence, to a first image sensor. A white light source is configured to emit white light during white light imaging. A second filter is configured to detect and permit passage of optical signals, responsive to illumination of the target surface with the white light and having a wavelength in the visible light range, to a second image sensor. And, a processor is configured to receive the detected fluorescent and white light optical signals and to output a representation of the target surface to a display based on the detected optical signals.

In accordance with another aspect of the present disclosure, a portable, modular handheld imaging system is provided. The modular system comprises a first housing portion and a second housing portion. The first housing portion includes at least one excitation light source configured to emit excitation light during fluorescent imaging; a first filter configured to detect and permit passage of optical signals, responsive to illumination of a target surface with the excitation light and having a wavelength corresponding to one or more of bacterial fluorescence, bacterial autofluorescence, tissue fluorescence, and tissue autofluorescence, to a first image sensor; a white light source configured to emit white light during white light imaging, and a second filter configured to detect and permit passage of optical signals, responsive to illumination of the target surface with the white light and having a wavelength in the visible light range, to a second image sensor. The second housing portion is configured to releasably receive the first housing portion and includes a display and a processor configured to receive the detected fluorescent and white light optical signals and to output a representation of the target surface to the display based on the detected optical signals.

In accordance with an additional aspect of the present disclosure, a portable, modular handheld imaging system kit is provided. The kit includes a plurality of optical housing portions and a base housing portion. Each of the plurality of optical housing portions comprises at least one excitation light source configured to emit excitation light during fluorescent imaging; a first filter configured to detect and permit passage of optical signals, responsive to illumination of a target surface with the excitation light and having a wavelength corresponding to one or more of bacterial fluorescence, bacterial autofluorescence, tissue fluorescence, and tissue autofluorescence, to a first image sensor; a white light source configured to emit white light during white light imaging, and a second filter configured to detect and permit passage of optical signals, responsive to illumination of the target surface with the white light and having a wavelength in the visible light range, to a second image sensor. The base housing portion is configured to releasably receive, interchangeably, each of the plurality of optical housing portions. The base housing portion comprises a display, a power source configured to power the at least one excitation light source and the white light source, and a processor configured to receive the detected fluorescent and white light optical signals and to output a representation of the target surface to the display based on the detected optical signals.

In accordance with yet another aspect of the present disclosure, a method of operating a modular, handheld fluorescence-based imaging device is provided. The method includes selecting an optical housing comprising optical components including at last one excitation light source for fluorescence imaging and connecting the selected optical housing to a base body housing of the imaging device to provide power from a power source in the base body housing to the optical components in the optical housing. The method also includes illuminating a target with the at least excitation light source to cause one or more of a part, a component, and a biomarker of the illuminated portion of the target to fluoresce, to reflect light, or to absorb light and filtering optical signals responsive to the illumination of the target with the excitation light, wherein filtering the plurality of optical signals includes preventing passage of reflected excitation light and permitting passage of optical signals having a wavelength corresponding to one or more of bacterial fluorescence, bacterial autofluorescence, tissue autofluorescence and exogenous tissue fluorescence through a fluorescent filter contained in the optical housing. The method further includes detecting the filtered optical signals with an image sensor contained in the optical housing, and displaying the detected, filtered signals on at least one display of the base body housing as a composite image of the illuminated portion of the target, the composite image comprising fluorescent representations of various tissue components present in the illuminated portion of the target.

BRIEF DESCRIPTION OF DRAWINGS

The present disclosure can be understood from the following detailed description either alone or together with the accompanying drawings. The drawings are included to provide a further understanding and are incorporated in and constitute a part of this specification. The drawings illustrate one or more exemplary embodiments of the present disclosure and together with the description serve to explain various principles and operations.

DETAILED DESCRIPTION

Figure 1:
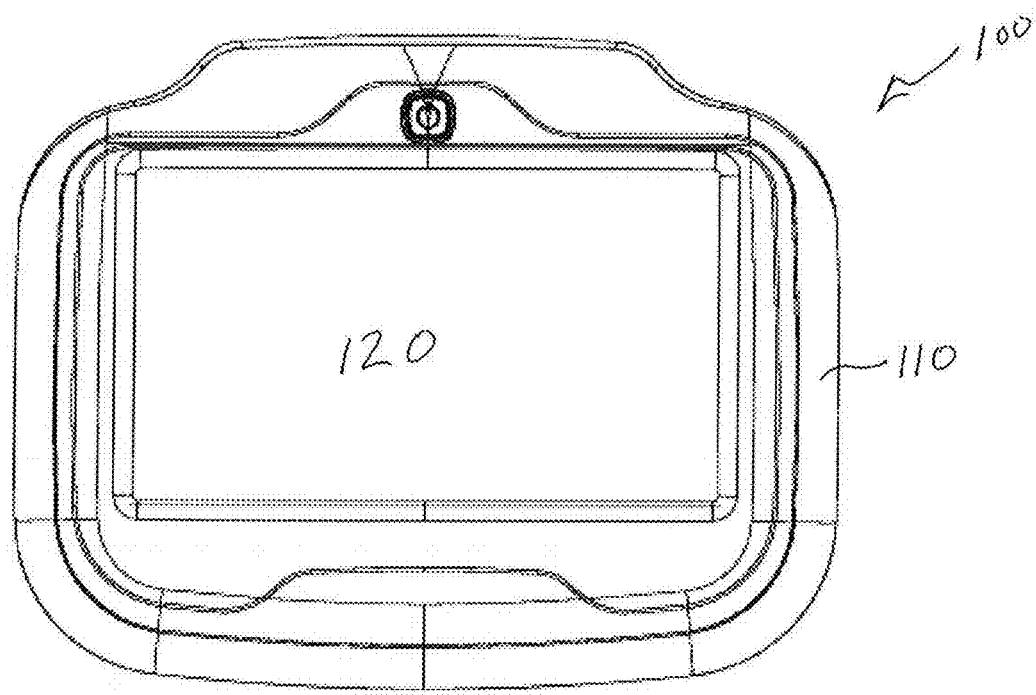
FIG. 1 is a front view of a first embodiment of a modular, handheld imaging device according to the present disclosure.
Figure 2:
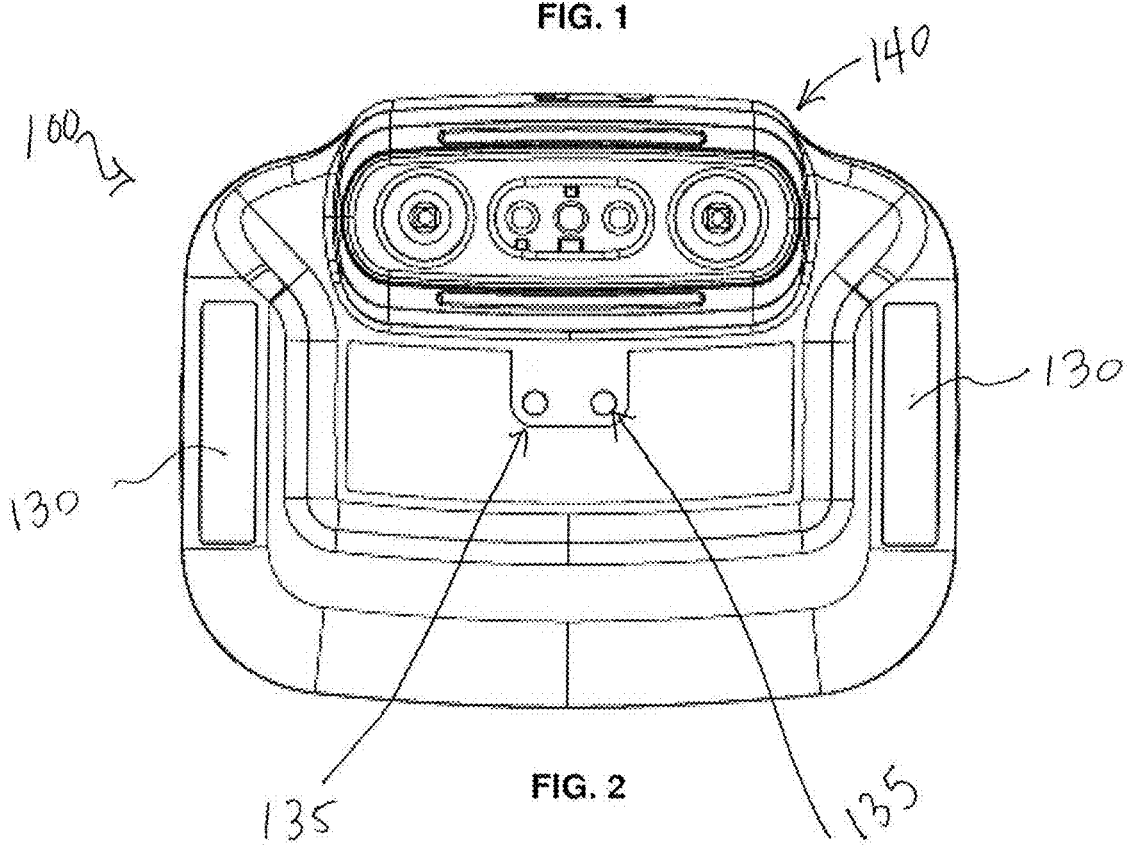
FIG. 2 is a back view of the modular, handheld imaging device of FIG. 1.
Figure 3:
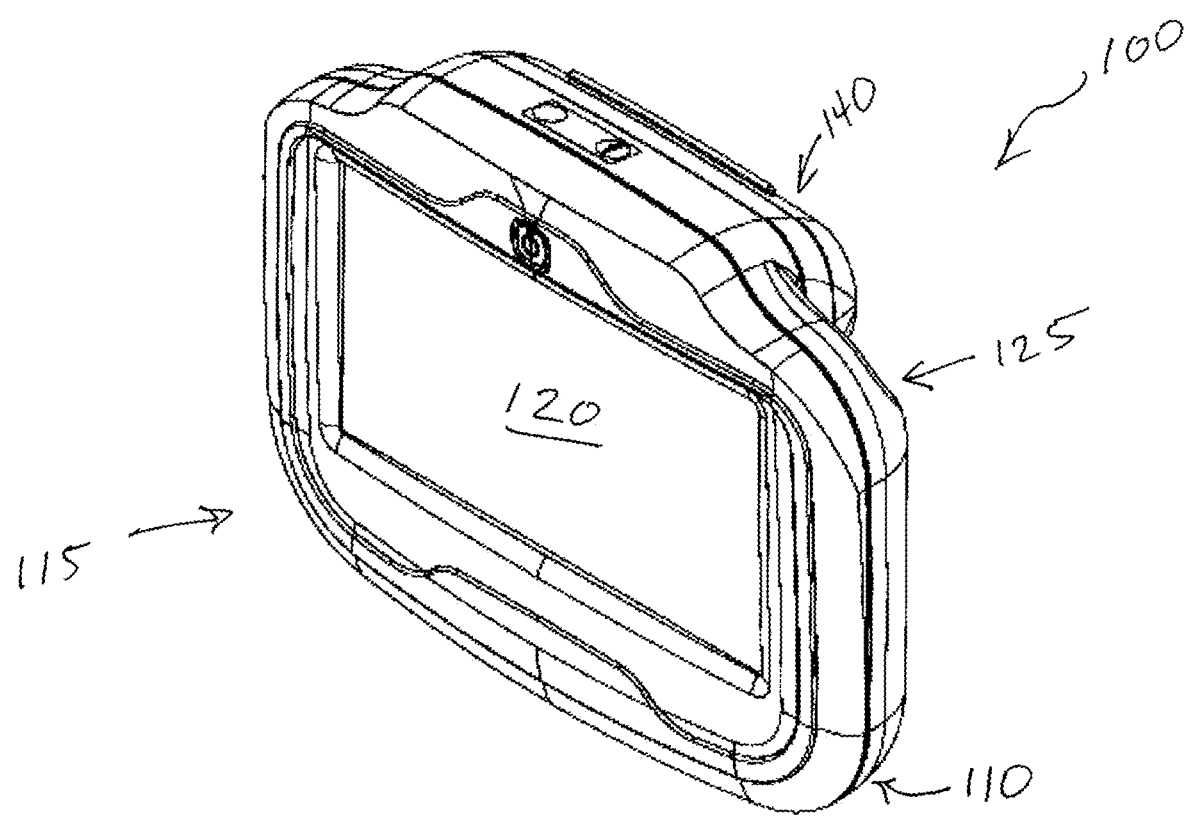
FIG. 3 is a front perspective view of the modular, handheld imaging device of FIG. 1.

Wound progression is currently monitored manually. The National Pressure Ulcer Advisory Panel (NPUAP) developed the Pressure Ulcer Scale for Healing (PUSH) tool that outlines a five-step method of characterizing pressure ulcers. This tool uses three parameters to determine a quantitative score that is then used to monitor the pressure ulcer over time. The qualitative parameters include wound dimensions, tissue type, and the amount of exudate or discharge, and thermal readings present after the dressing is removed. A wound can be further characterized by its odor and color. Such an assessment of wounds currently does not include critical biological and molecular information about the wound. Therefore, all descriptions of wounds are somewhat subjective and noted by hand by either the attending physician or the nurse.

What is desirable is a robust, cost-effective non-invasive and rapid imaging-based method or device for objectively assessing wounds for changes at the biological, biochemical and cellular levels and for rapidly, sensitively and non-invasively detecting the earliest presence of bacteria/microorganisms within wounds. Such a method or device for detection of critical biological tissue changes in wounds may serve an adjunctive role with conventional clinical wound management methods in order to guide key clinico-pathological decisions in patient care. Such a device may be compact, portable and capable of real-time non-invasive and/or non-contact interrogation of wounds in a safe and convenient manner, which may allow the handheld imaging device to fit seamlessly into routine wound management practice and be user friendly to the clinician, nurse and wound specialist. The handheld imaging device may also be used in the home-care environment (including self-use by a patient), as well as in military battlefield environments. In addition, such an image-based device may provide an ability to monitor wound treatment response and healing in real-time by incorporating valuable 'biologically-informed' image-guidance into the clinical wound assessment process. This may ultimately lead to potential new diagnosis, treatment planning, treatment response monitoring and thus 'adaptive' intervention strategies which may permit enhancement of wound-healing response at the individual patient level. Precise identification of the systemic, local, and molecular factors underlying the wound healing problem in individual patients may allow better tailored treatment.

The MolecuLight i:X device has made strides in addressing many of the issues raised above. The MolecuLight i:X device allows clinicians to quickly, safely and easily visualize bacteria and measure wounds at the point of care. The bases of the MolecuLight i:X device and methods of use are described in U.S. Pat. No. 9,042,967, which is a national stage application of PCT/CA2009/000680, filed internationally on May 20, 2009, which claims benefit to U.S. Provisional Application No. 61/054,780, filed May 20, 2008, the entire content of each of which is incorporated by reference herein.

Another imaging device, disclosed for use in cancer visualization, is disclosed in U.S. Provisional Application No. 62/625,983 (filed Feb. 3, 2018) entitled "Devices, Systems, and Methods for Tumor Visualization and Removal" and U.S. Provisional Application No. 62/625,967 (filed Feb. 3, 2018) entitled "Devices, Systems, and Methods for Tumor Visualization and Removal," and International Patent Application No. PCT/CA2019/000015, filed Feb. 1, 2019 and entitled "Devices, Systems, and Methods for Tumor Visualization and Removal," the entire contents of each of which are incorporated by reference herein. Although disclosed in the context of visualizing cancer, the systems and methods disclosed relate to visualizing and imaging tissue autofluorescence and tissue fluorescence and the details regarding the construction, functionality, and operation of exemplary devices described therein may be similar to or the same as parts of systems described herein.

The MolecuLight i:X device and the device disclosed in the present application make use of tissue autofluorescence imaging which provides a unique means of obtaining biologically relevant information of normal and diseased tissues in real-time, thus allowing differentiation between normal and diseased tissue states. An autofluorescence imaging device may be useful for rapid, non-invasive and non-contact real-time imaging of wounds, to detect and exploit the rich biological information of the wound to overcome current limitations and improve clinical care and management.

In the present application, systems, methods and devices for fluorescence-based imaging are disclosed. One embodiment of the device is a portable optical digital imaging device. The device may utilize a combination of white light (WL) imaging, fluorescence (FL) imaging, infrared (IR) imaging, thermal imaging, and/or three-dimensional mapping, and may provide real-time wound imaging, assessment, recording/documenting, monitoring and/or care management. The device may be hand-held, compact and/or light-weight. For example, the device may comprise at least one excitation light source configured to emit excitation light during fluorescent imaging; a first filter configured to detect and permit passage of optical signals, responsive to illumination of a target surface with the excitation light and having a wavelength corresponding to one or more of bacterial fluorescence, bacterial autofluorescence, tissue fluorescence, and tissue autofluorescence, to a first image sensor; a white light source configured to emit white light during white light imaging; a second filter configured to detect and permit passage of optical signals, responsive to illumination of the target surface with the white light and having a wavelength in the visible light range, to a second image sensor; and a processor configured to receive the detected fluorescent and white light optical signals and to output a representation of the target surface to a display based on the detected optical signals. This device and method may be suitable for monitoring of wounds in humans and in animals.

In another exemplary embodiment, the device may be a modular handheld imaging device. In such an embodiment, the device comprises a base body portion, also referred to herein as a base portion or a base housing, and an optical portion also referred to herein as an optical housing or optical housing portion. The optical portion is releasably received by the base body portion and is interchangeable with other optical portions, each optical portion being configured for a particular application or to capture particular characteristics of and optical information from the target being imaged. Thus, a user will select an optical housing based upon the capabilities desired for imaging in a given situation.

The modular handheld imaging device may be packaged and/or sold as a part of a kit, where the base body portion and two or more optical portions are provided, the optical properties of each optical portion differing from each other and any other optical housings. The properties that may vary from one optical housing to another include the following non-limiting examples, which may be included in any combination in each optical housing: number of image sensors, number of image sensors configured for white light imaging (i.e., combined with filter for white light imaging); number of image sensors configured for fluorescent imaging, wherein different image sensors for fluorescent imaging may be paired with different filters to permit passage of different ranges of fluorescent emissions, wherein each range is configured to capture a particular characteristic of a target (e.g., vasculature or microvasculature, collagen, elastin, blood, bone, bacteria, malignancy, lymphatics, immune cells, adipose tissues, cartilage, tendons, nerves, gastrointestinal tissues, skin, pre-malignant or benign tissues, bodily fluids, urine, blood, saliva, tears, mucus, mucosal tissues, dermal tissues, and exogenous fluorescent agents, drugs, etc.).

The image sensors are configured to capture still images or video.

The number and type of excitation light sources may vary between optical housings as well. The excitation light sources are configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, about 900 nm-about 950 nm, about 950 nm-about 1000 nm, and/or combinations thereof. The shape of the optical housing may also vary from one housing to another, depending upon the particular application. For example, specialized shapes may be used for particular applications such as, for example, accessing confined anatomical spaces such as recesses, oral cavities, nasal cavities, anal area, abdominal area, ears, etc. In such cases, the optical housing may have the form of an endoscopic attachment. The materials forming the optical housing may vary from one housing to another. For example, the housing may have a flexible patient-facing portion or a rigid patient facing portion, dependent upon the application in which the imaging device is to be used. The optical housing may be made waterproof or water resistant in some embodiments. The housing may, in some embodiments, be made of materials that are inherently resistant to bacterial growth or be made of a material with a surface texture or topology that is resistant to microbial growth, e.g., roughened nanosurface. The size of the optical housing may vary depending upon the size and number of components contained therein. Various exemplary embodiments of the optical housings may also include, in any combination, features such as an ambient light sensor, a range finder, thermal imaging sensors, structured light emitters, an infrared radiation source and detector to be used for three-dimensional imaging, lasers for taking measurements, etc. Additionally or alternatively, the imaging device may also and have an external channel embedded in the housing to enable delivery of a tool such as a biopsy forcep, optical fiber spectroscopy probe or other implement that requires (FL) image guided targeting to collect tissue, ablate tissue, cauterize tissue or interrogate tissue that is fluorescent.

The base body portion/base housing includes an interface configured to releasably receive the optical housing. The optical housing includes a portion configured to be received into the base body portion in a manner that provides electrical and power connections between the components in the optical housing and the battery and processor in the base body portion. The connection will enable data transfer between the optical housing and the base, which contains a processor configured to receive data from the image sensor. Additionally, the base can be connected to a PC to store or analyze the data form the modular imaging device.

In various exemplary embodiments, the base body portion includes a heat sink. In one example embodiment, the heat sink forms a lip around the opening in the base body portion that is configured to receive the optical housing.

In various example embodiments, the modular imaging device includes the following elements in various configurations:

FL Camera Sensor—A camera sensor configured to detect fluorescent wavelengths is used in fluorescent imaging mode (FL). Light incident on this sensor passes through a dual band filter to permit visualization and capture of red and green fluorescent signals that may be present, for example, signals generated responsive to illumination of a target with excitation light. In some embodiments, the filter may be configured to recognize additional fluorescent signals or fewer fluorescent signals.

WL Camera 1—A first white light (WL) camera sensor is used when the modular imaging device is in a white light (WL) imaging mode. Light incident on this sensor passes through a shortpass filter to allow the sensor to image visible light wavelengths. The shortpass filter blocks infrared (IR) light that may be present in the clinical environment. The shortpass filter also blocks IR emitted by a range finder, if present.

WL Camera 2—A second WL image sensor/camera sensor may be used as part of a stereoscopic or 3D imaging (target depth) configuration of the modular imaging device.

Light incident on this sensor passes through a shortpass filter to allow the sensor to image visible light wavelengths. The shortpass filter blocks infrared (IR) light that may be present in the clinical environment. The shortpass filter also blocks IR emitted by a range finder, if present. When present, second WL camera sensor must be aligned with the first WL camera sensor.

Display—A high resolution, wide color gamut display with touchscreen function may be provided. The touchscreen function allows users to manipulate images and also allows the display to act as a primary user interface (UI) for the clinician/device operator, allowing the input of patient information which may be collated or registered in some manner with images taken, either on the camera or when the information is uploaded to the cloud or other storage.

Battery—A rechargeable battery, such as a rechargeable lithium ion battery with integrated gas gauging function may be used to power the modular imaging device.

As will be understood, other types of batteries may be used or other power sources used.

Speaker—A speaker on the modular imaging device may be used to communicate with the user and may also generate camera click sound and/or other sounds which improve the user experience.

Battery Status LED—Indicates low battery condition and battery state of charge during charging operation.

System Status LED—Indicates system status through use of on/off or different colors, provides indication of system OK/operational or indicates presence of internal system issue.

Wi-Fi Antenna—Enables WIFI communications. WIFI communications used for cloud storage of images, field update of system software, and managing pay-per-use usage.

FL LEDs—The light sources of the modular device may comprise LEDs. In one example, excitation light, such as fluorescent excitation light, may be generated by fluorescent (FL) LEDs. The fluorescent excitation light can be used to elicit fluorescence from bacteria, i.e., as a response to illumination with the excitation light. LED current is controlled by closed loop control where the set point of the control loop is managed by the MCU. Nominal FL LED drive current set-point is established during the device manufacturing process in order to satisfy minimum on-target optical irradiance and uniformity requirement. LED optical efficiency is temperature dependent. Temperature sensors measure printed circuit board (PCB) temperature near the LEDs, which is used as an input to a control loop which adjusts the nominal drive current setpoint to compensate for LED temperature dependent irradiance efficiency change. As will be understood, other types of fluorescent light sources may be used instead of or in addition to FL LEDs.

An ambient light sensor is provided to monitor the ambient light in the imaging environment near the imaging target. Fluorescence (FL) imaging requires an adequately dark environment to obtain useful images. The ambient light sensor is used to provide feedback to the clinician on the ambient light level. Ambient light level prior to the system going into FL imaging mode can be stored in picture metadata. The light level could be useful during post analysis. The measured ambient light level could also be useful during white light imaging mode to enable the WL torch or control its intensity. The ambient light sensor may be configured to indicate to a user when the imaging environment is sufficiently dark to take a fluorescent image. This may take the form of providing an indication that the imaging environment is satisfactory and/or unsatisfactory, depending upon the imaging mode.

Range Finder—A range finder may be used to measure the distance between the camera sensor and target being imaged. The minimum on target blue light irradiance and uniformity is valid within a range of camera to target distances. The range finder provides feedback to the clinician/user to guide them on imaging at the correct distance by providing an indication that an appropriate distance has been reached. The target distance can be stored in picture metadata. The target distance could be useful to a sticker detection algorithm, which may be used in measuring processes, for determining the minimum and maximum expected sticker size in sensor pixels which is a function of distance between the sticker and camera sensor. In some embodiments, a change in measured target distance could be used to initiate a camera sensor refocus action.

Torch LED—One or more white light sources may be provided to illuminate the target during white light imaging mode. White light sources may include one or more white light LEDs. Other sources of white light may be used in addition to or instead of LEDs.

USB-C Port—A USB-C port may be provided to use for battery charging, factory load of software, factory test and calibration of device, and picture download. Additional or alternate ports may be provided for transfer of information and/or charging.

An exemplary embodiment of a modular handheld imaging device 100 is shown in FIGS. 1-5B. As shown in FIGS. 1-5B, in some example embodiments, a base body portion 110 of device 100 may have a generally square or rectangular shape. A front, or user-facing side 115 of the base body portion 110 includes a display screen 120 for displaying images and videos captured by the device. Although depicted as square or rectangular, the device may take on any shape that will reasonably support a display screen such as a touchscreen display. In addition to disclosing images captured by the imaging device 100, the display screen also operates as a user interface, allowing the user to control functions of the device via touchscreen input.

Figure 4:
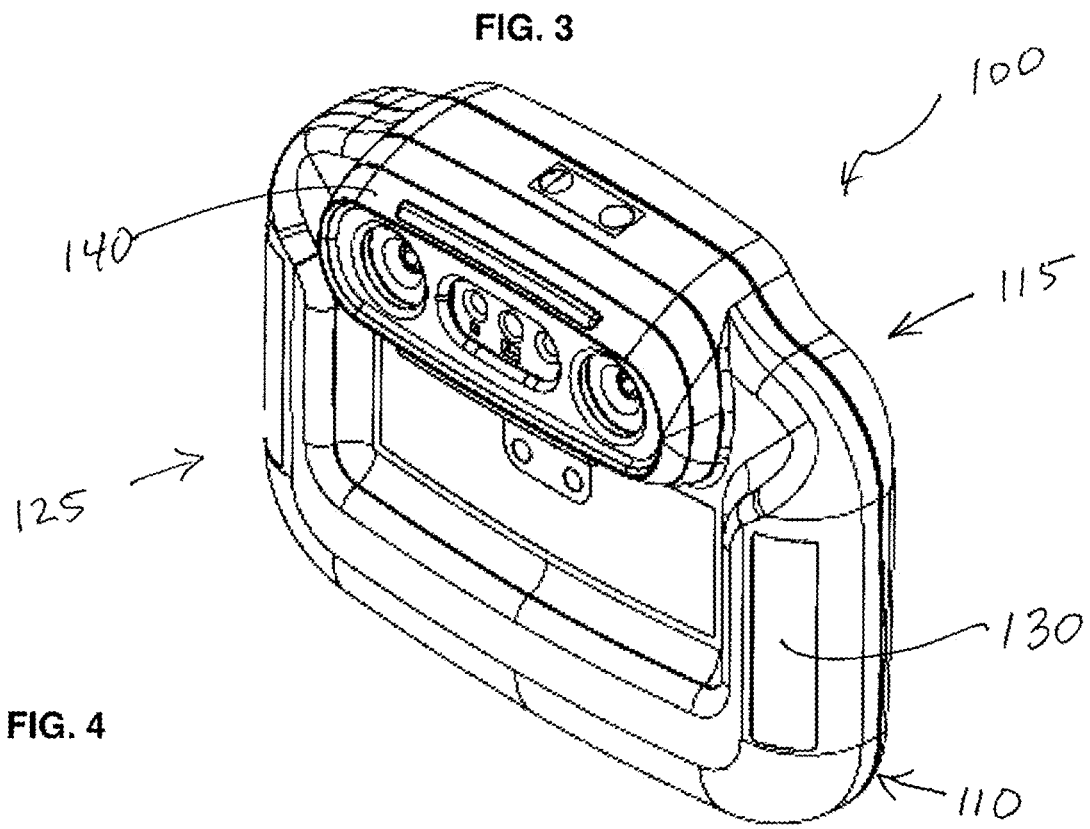
FIG. 4 is a rear perspective view of the modular, handheld imaging device of FIG. 1.

Positioned on an opposite side of the device, on the patient-facing side 125 of the device, may be handhold areas 130 configured to facilitate a user holding the device during imaging. As illustrated in FIG. 4, the handhold areas may comprise protrusions or areas that extend away from the base body portion 110 sufficiently to allow a user's fingers to grip or wrap around the protrusions. Various other types of handholds as well as alternative positioning of the handholds may be used. One consideration in the position of such handholds is the ability of the user to balance the imaging device while using the device for imaging and while inputting commands via the touchscreen display. Weight distribution of the imaging device will also be a consideration to provide a user-friendly and ergonomic device. The patient facing-side 125 of the device may also incorporate contacts 135 for wireless charging of the device.

As illustrated in FIGS. 11A-11E, a charging station 136 may be provided for wireless charging of device 100. As shown in the example embodiment, charging station 136 may include contacts such as contact pins 137 for wireless charging of device 100. The contact pins 137 may be spring loaded and may be separated from one another in a manner that prevents a short by inadvertent placement of other objects on the contact pins 137 (i.e., small metallic objects). In one example, a raised portion of the surface of the charging station 136, such as a protrusion, may separate the contact pins 137. The charging station 136 may also include an indicator light 138 that will engage/come on when the device 100 is properly positioned on the charging station 136 to charge. Additionally or alternatively, the indicator light 138 may indicate when the device 100 is fully charged.

Figure 5A:
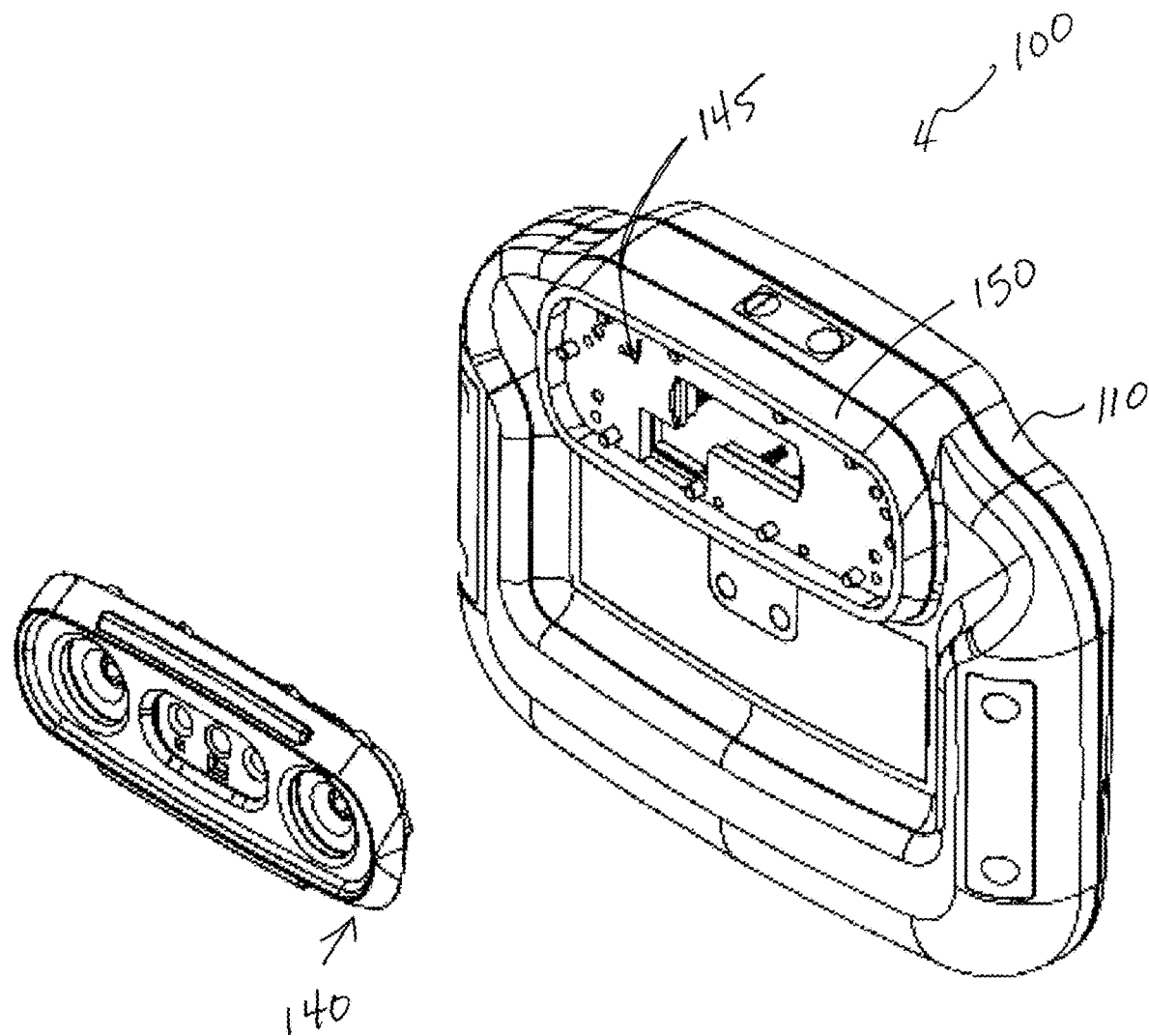
FIG. 5A is a perspective view of a first optical housing detached from a base housing of a second embodiment of a modular, handheld imaging system according to the present disclosure.
Figure 5B:
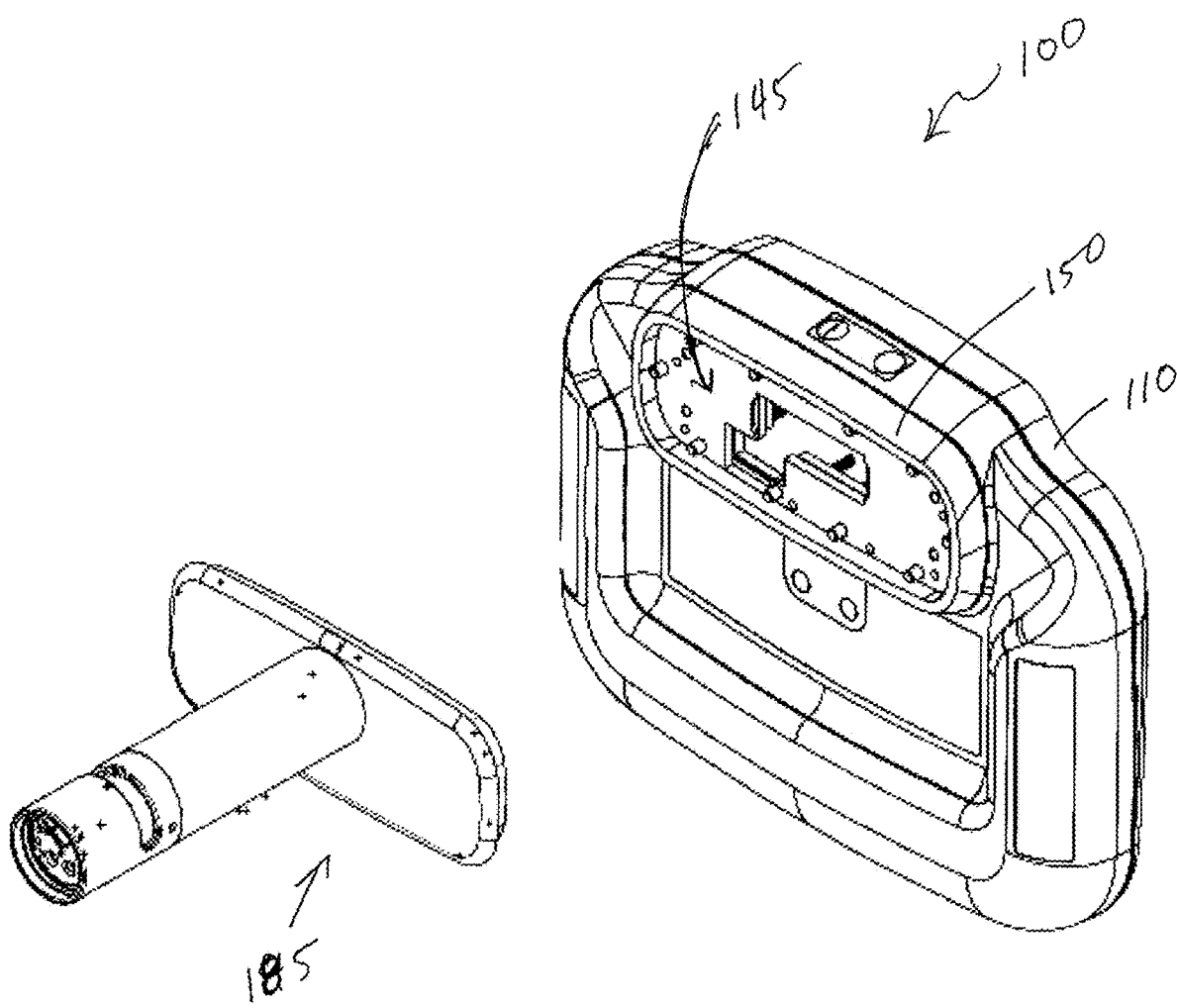
FIG. 5B is a perspective view of a second optical housing detached from the base housing of a third embodiment of a modular, handheld imaging system according to the present disclosure.
Figure 6:
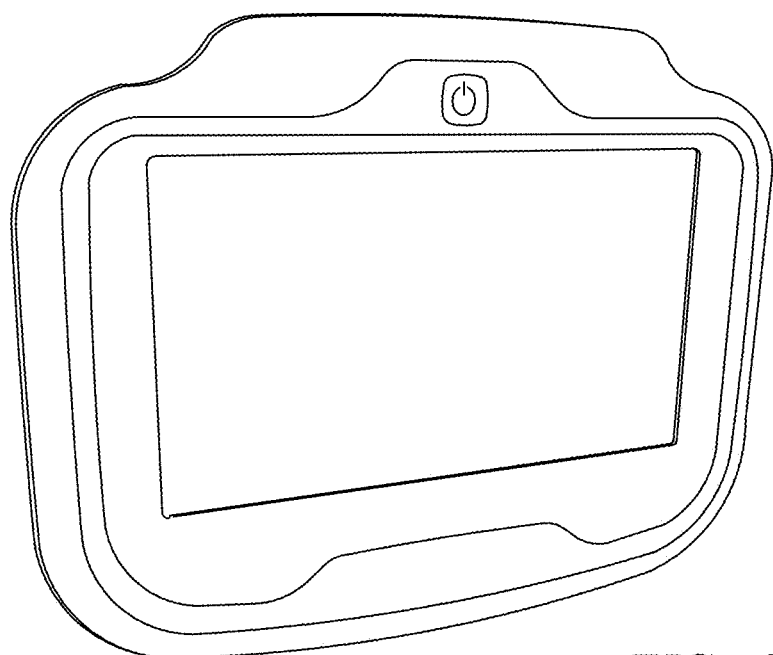
FIG. 6 is a front view of a rendering of a fourth embodiment of a modular, handheld imaging device according to the present disclosure.
Figure 7:
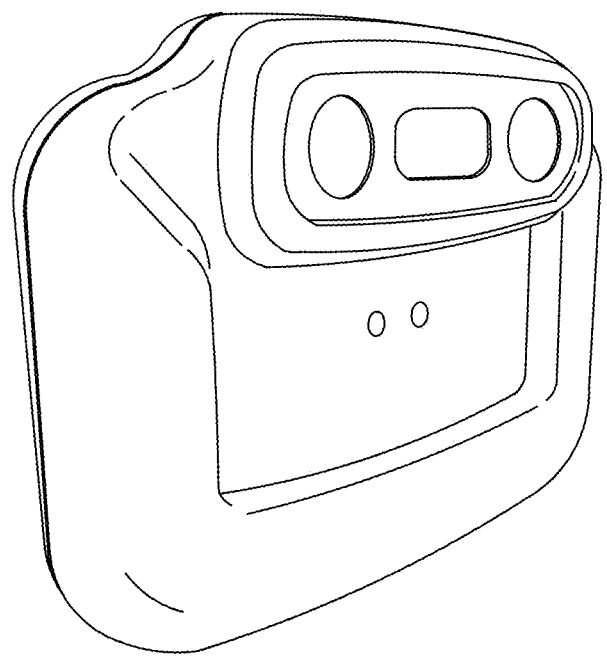
FIG. 7 is a rear view of a rendering of the modular, handheld imaging device of FIG. 6 in accordance with the present disclosure.
Figure 8:
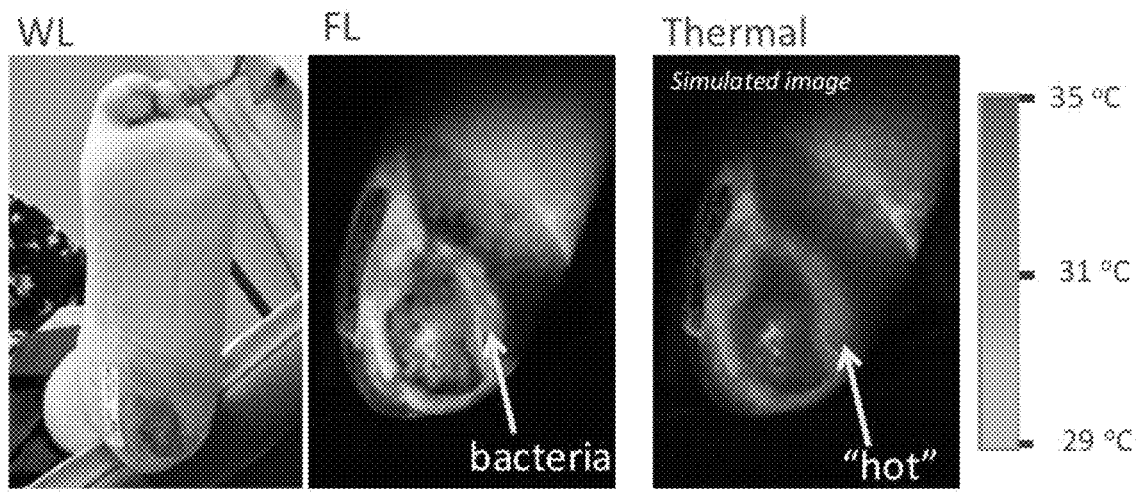
FIG. 8 are examples of white light (WL), fluorescent (FL), and thermal images acquired with exemplary embodiments of a modular, handheld imaging device in accordance with the present disclosure.
Figure 9:
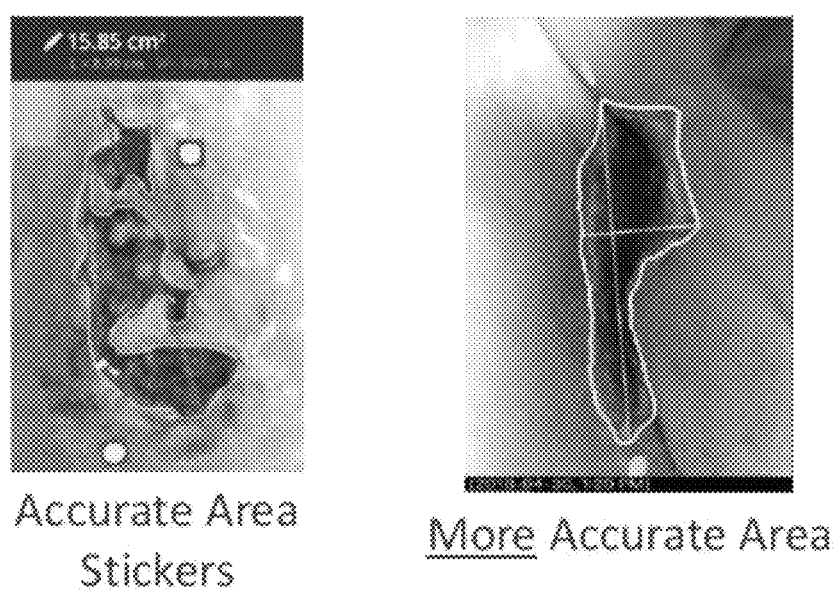
FIG. 9 are examples of measurements taken with exemplary embodiments of a modular, handheld imaging device in accordance with the present disclosure.
Figure 10A:
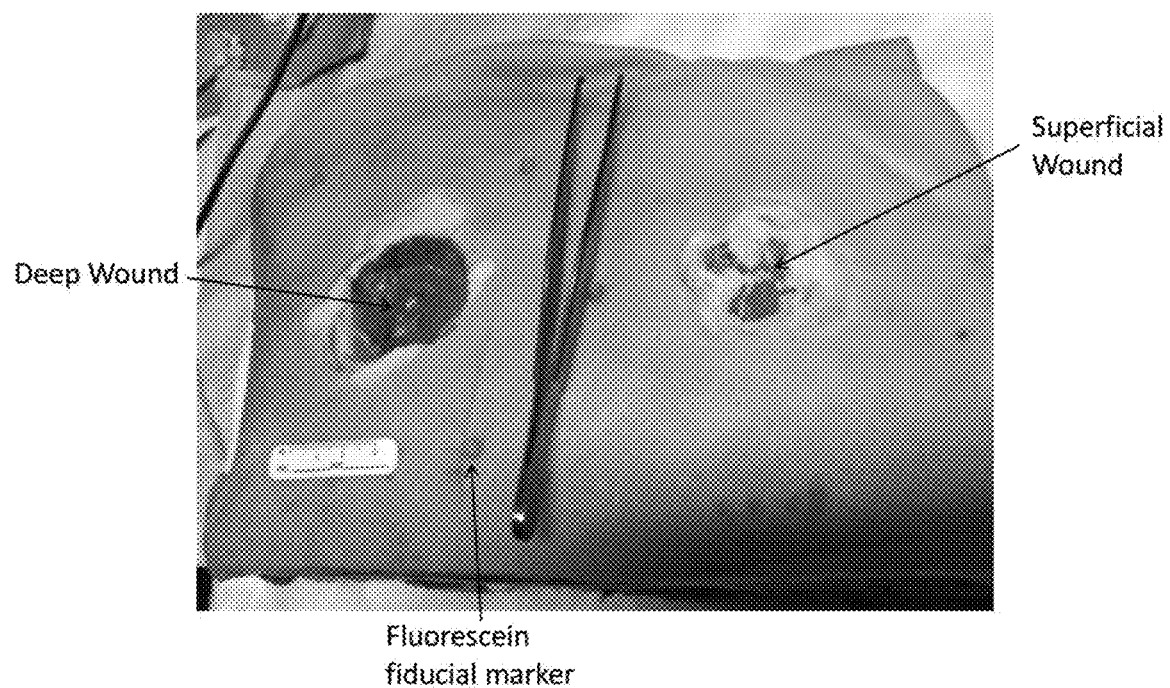
FIGS. 10A-10D are examples of images acquired and created in the process of forming a three-dimensional fluorescent image of a target with an exemplary embodiment of a modular, handheld imaging device in accordance with one aspect of the present disclosure.
Figure 10B:
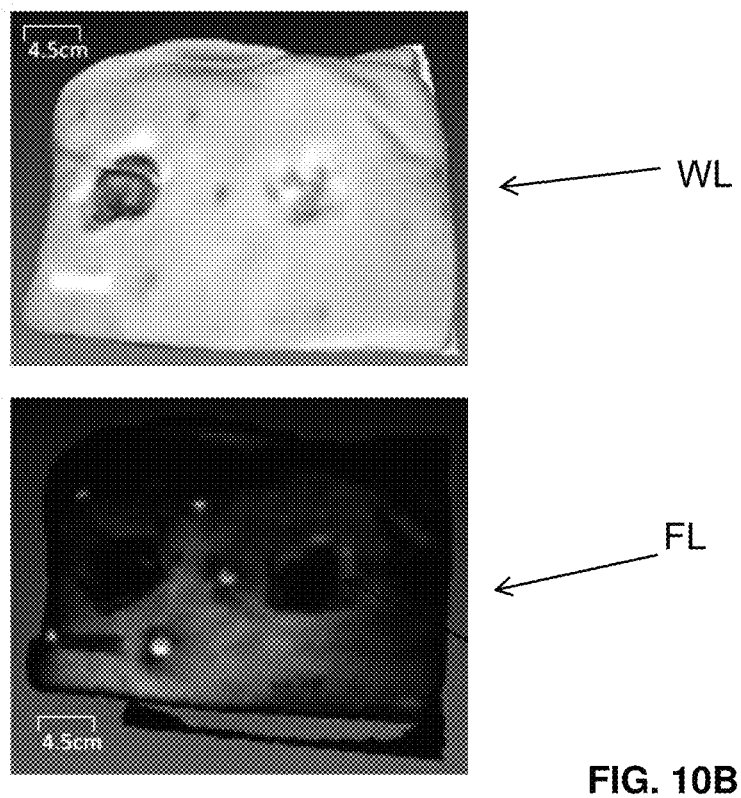
Figure 10C:
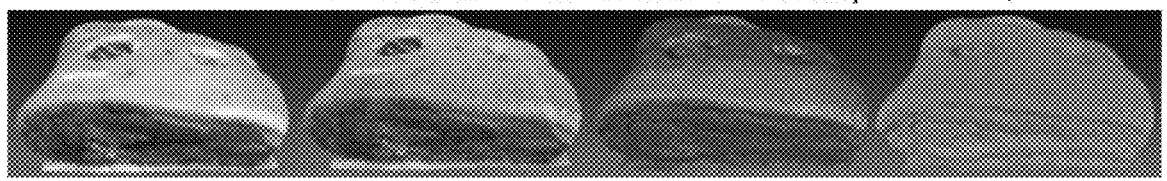
Figure 10C:
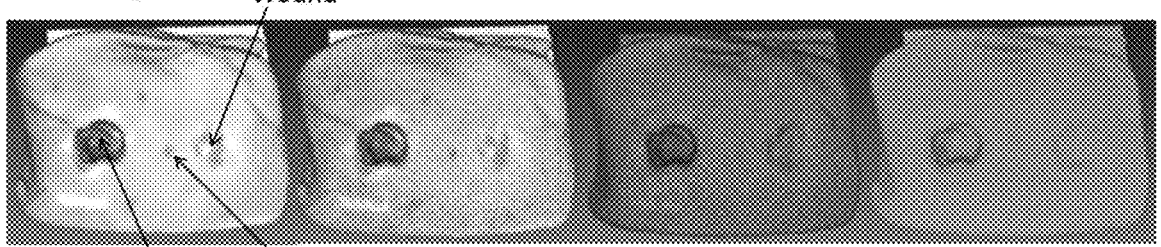
Figure 10D:
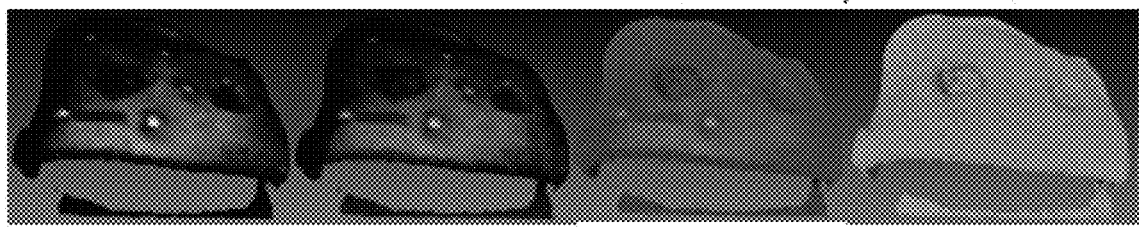
Figure 10D:
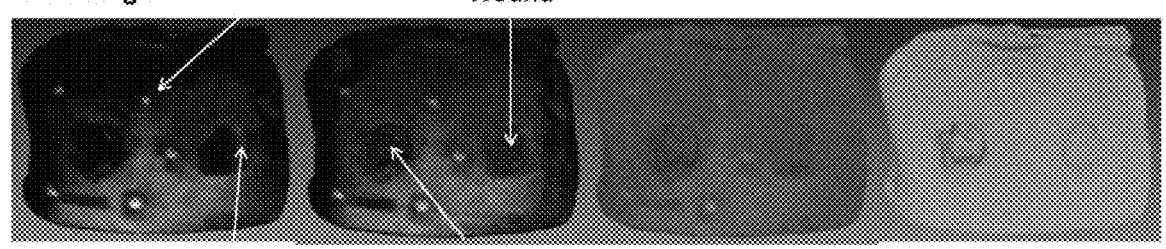
Figure 11A:
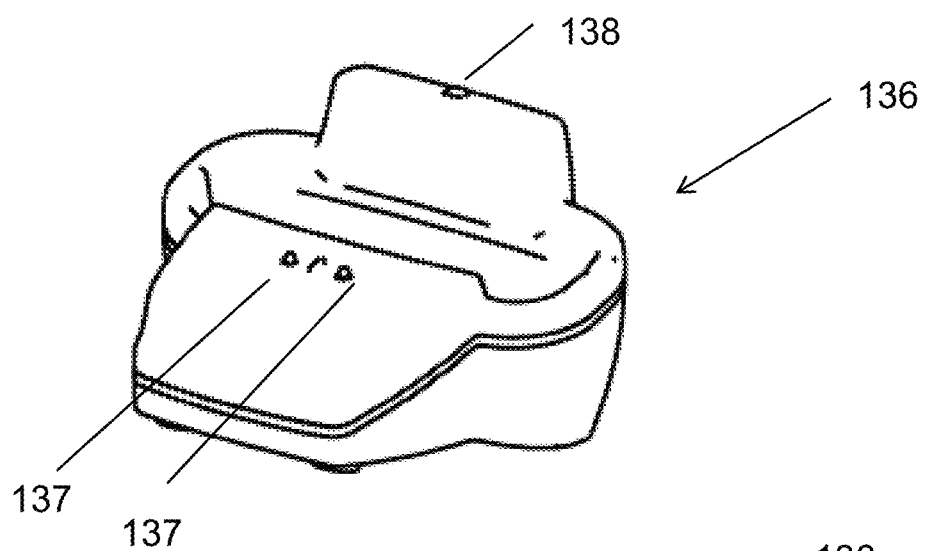
FIGS. 11A-11E show a charging station alone (FIGS. 11A-11C) and in use with an imaging device (FIGS. 11D and 11E) in accordance with the present disclosure.
Figure 11B:
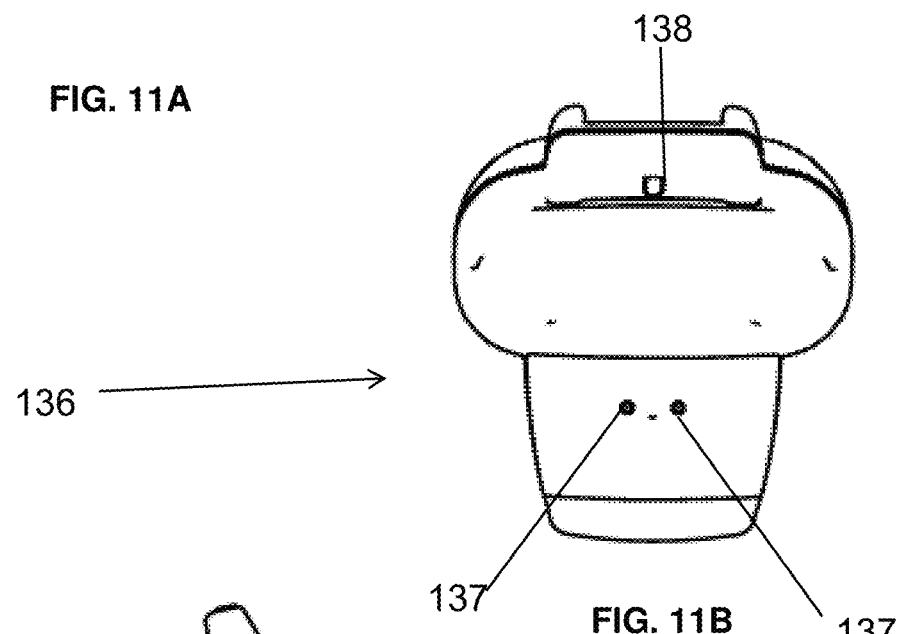
Figure 11C:
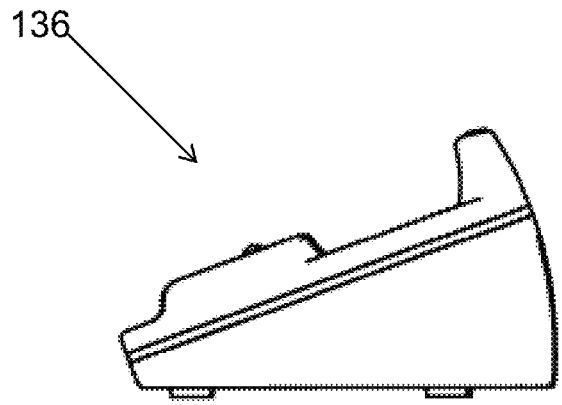
Figure 11D:
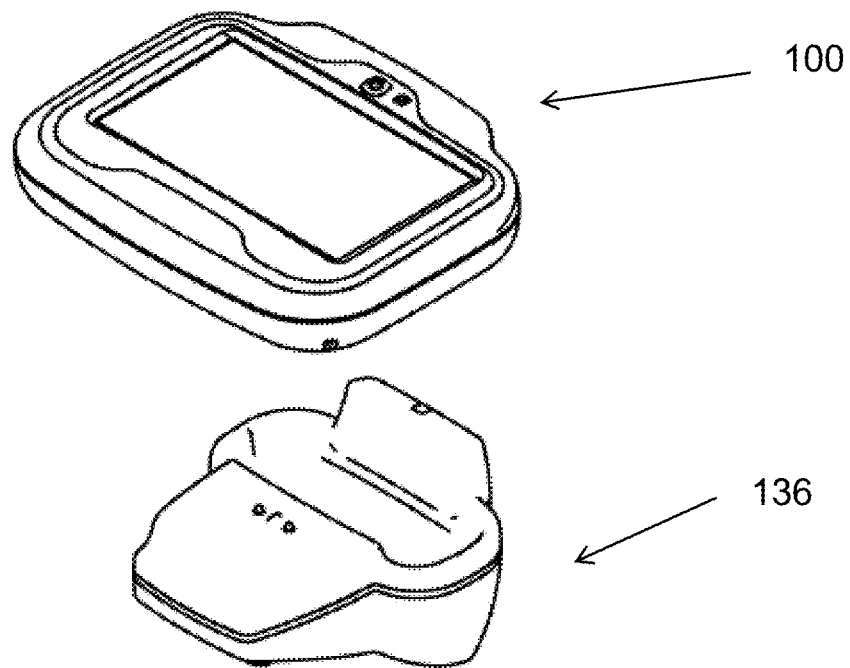
Figure 11E:
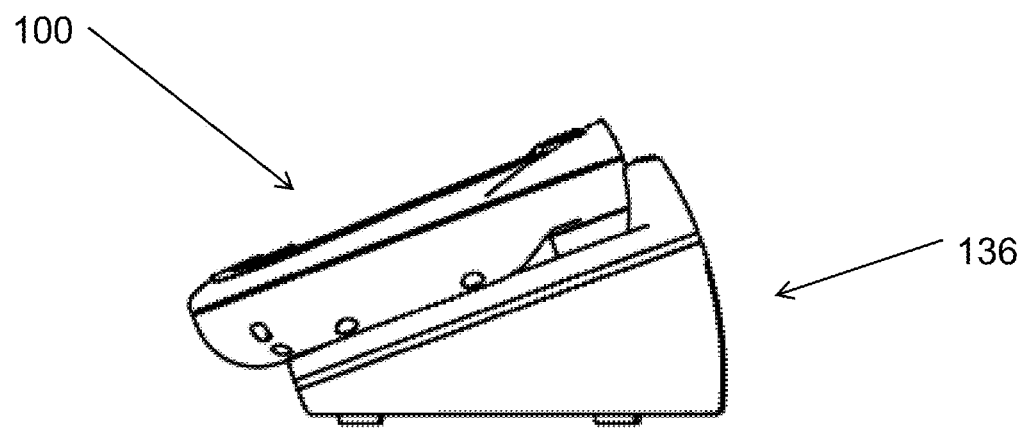

In accordance with one aspect of the present disclosure, the patient-facing side 125 of device 100 also includes an optical housing 140. Optical housing portion 140 may be detachable from base body portion 110 as illustrated in FIGS. 5A-5B. Optical housing portion 140 is illustrated as a rectangular housing configured to be received in a rectangular opening 145 on the base body portion 110. However, both optical housing portion 140 and opening 145 may take other shapes, such as for example square, oblong, oval or circular. Further, optical housing portion 140 may not have the same shape as opening 145 but instead a connector element having the same shape as or otherwise configured to be received in opening 145 of base body portion 110 may be used as a bridge to connect optical housing portion 140 to base body portion 110. The opening 145 is configured to releasably receive the optical housing portion 140. When the optical housing portion 140 is positioned in opening 145, it may be locked into position such that optical housing portion 140 is locked to base body portion 110. In this configuration, electrical contacts are made between base body portion 110 and the optical components contained in optical housing portion 140 and the components in the optical housing portion are powered by a power source, such as a battery, contained in the base body portion 110.

In various example embodiments, the base body portion 110 includes a heat sink 150. In one example embodiment, the heat sink 150 forms a lip around the opening 145 in the base body portion 110 that is configured to receive the optical housing portion 140.

As illustrated in FIGS. 5A and 5B, the optical housing 140 may take on different shapes or configurations. For example, as shown in FIG. 5A, the optical housing portion 140 has a generally flat, oblong shape. The optical components are arranged in a generally linear manner across a width of the optical housing. FIG. 5B shows a second optical housing 185 which includes an endoscope portion 190. Unlike optical housing portion 140, the optical components contained in second optical housing 185 are contained in a distal tip 195 of the endoscope portion 190 of the second optical housing 185 and are not arranged in a linear manner. The arrangement of the optical components will vary in each optical housing based upon the size and shape of the optical housing as well as the number and type of optical components contained in a given housing.

The optical housing portion 140 can include various optical components configured to facilitate the collection of optical signals from a target being imaged. The properties that may vary from one optical housing to another include the following non-limiting examples, which may be included in any combination in each optical housing: total number of image sensors, number of image sensors configured for white light imaging (i.e., combined with filter for white light imaging); number of image sensors configured for fluorescent imaging, wherein different image sensors for fluorescent imaging may be paired with different filters to permit passage of different ranges of fluorescent emissions, wherein each range is configured to capture a particular characteristic of a target (e.g., vasculature or microvasculature, collagen, elastin, blood, bone, bacteria, malignancy, healthy or diseased cartilage, ligaments, tendons, connective tissue, lymphatics, nerve, muscle etc.).

The optical housing portion 140 can include one or more excitation light sources. An excitation light source may provide a single wavelength of excitation light, chosen to excite tissue autofluorescence emissions and as well as fluorescence emissions of induced porphyrins in tumor/cancer cells. Additionally or alternatively, an excitation light source may provide a wavelength of excitation light chosen to excite bacterial autofluorescence emissions and/or exogenous fluorescence emissions of one or more of tissue and bacteria in a wound. In one example, the excitation light may have wavelengths in the range of about 350 nm-about 600 nm, or 350 nm-about 450 nm and 550 nm-about 600 nm, or, for example 405 nm, or for example 572 nm.

Alternatively, the excitation light source may be configured to provide two or more wavelengths of excitation light. The wavelengths of the excitation light may be chosen for different purposes, as will be understood by those of skill in the art. For example, by varying the wavelength of the excitation light, it is possible to vary the depth to which the excitation light penetrates a surface of a target such as a surgical bed or a wound. As depth of penetration increases with a corresponding increase in wavelength, it is possible to use different wavelengths of light to excite tissue below the surface of the target surface. In one example, excitation light having wavelengths in the range of 350 nm-450 nm, for example 405 nm, and excitation light having wavelengths in the range of 550 nm to 600 nm, for example 572 nm, may penetrate target tissue to different depths, for example, about 500 μm-about 1 mm and about 2.5 mm, respectively. This will allow the user of the device, for example a doctor, a surgeon or a pathologist, to visual tissue cells at the surface of the target and the subsurface of the target. Additionally or alternatively, an excitation light having a wavelength in the near infrared/infrared range may be used, for example, excitation light having a wavelength of between about 750 nm and about 800 nm, for example 760 nm or 780 nm, may be used. In addition, to penetrating the tissue to a deeper level, use of this type of light source may be used in conjunction with a second type of imaging/contrast agent, such as for example infrared dye (e.g., IRDye 800, ICG). This will enable, for example, visualization of vascularization, vascular perfusion, and blood pooling in the target tissue. In addition, the utility of visualizing vascular perfusion be to improve anastomosis during reconstruction or to observe healing of the wound.

The imaging device 100 may include additional light sources, such as a white light source for white light (WL) imaging of the target surface. Use of white light provides anatomical context for other images, such as fluorescent images. The white light source may include one or more white light LEDs. Other sources of white light may be used, as appropriate. As will be understood by those of ordinary skill in the art, white light sources should be stable and reliable, and not produce excessive heat during prolonged use.

The base body portion 110 of the imaging device 100 may include controls to permit switching/toggling between white light imaging and fluorescence imaging. The controls may also enable use of various excitation light sources together or separately, in various combinations, and/or sequentially. The controls may cycle through a variety of different light source combinations, may sequentially control the light sources, may strobe the light sources or otherwise control timing and duration of light source use. The controls may be automatic, manual, or a combination thereof, as will be understood by those of ordinary skill in the art. As discussed above, the touchscreen display 120 of base body portion 110 may function as a user interface to allow control of the imaging device 100. Alternatively, it is contemplated that separate controls, such as hand-actuated controls, for example buttons, may be used instead of or in addition to touchscreen controls. Such hand-actuated controls may be positioned, for example, on the handgrips 130 to allow the user to easily actuate the controls while holding and using the imaging device.

The optical housing portion 140 of the imaging device 100 may also contain one or more optical imaging filters configured to prevent passage of reflected excitation light to the camera sensor(s). In one example, optical imaging filters can also be configured to permit passage of emissions having wavelengths corresponding to autofluorescence emissions of tissue cells and fluorescence emissions of the induced porphyrins in tissue cells. In another example, the device 100 may contain one or more optical imaging filters configured to permit passage of emissions corresponding to autofluorescence emissions of bacteria contained in the target as well exogenous fluorescence emissions of bacteria due to the use of contrast agents on the target surface. The imaging device 100 may also include filters configured to capture fluorescence and autofluorescence of both bacteria and tissues.

These optical filters may be selected to detect specific optical signals from the target/tissue/wound surface based on the wavelength of light desired. Spectral filtering of the detected optical signal(s) (e.g., absorption, fluorescence, reflectance) may also be achieved, for example, using a liquid crystal tunable filter (LCTF), or an acousto-optic tunable filter (AOTF) which is a solid-state electronically tunable spectral band-pass filter. Spectral filtering may also involve the use of continuous variable filters, and/or manual band-pass optical filters. These filters/filtering mechanisms may be placed in front of the imaging sensor to produce multispectral, hyperspectral, and/or wavelength-selective imaging of tissues.

The imaging device 100 may be modified by using optical or variably-oriented polarization filters (e.g., linear or circular combined with the use of optical wave plates) attached in a reasonable manner to the excitation/illumination light sources and an imaging sensor. In this way, the imaging device 100 may be used to image the target surface with polarized light illumination and non-polarized light detection or vice versa, or polarized light illumination and polarized light detection, with either white light reflectance and/or fluorescence imaging. This may permit imaging of wounds with minimized specular reflections (e.g., glare from white light imaging), as well as enable imaging of fluorescence polarization and/or anisotropy-dependent changes in connective tissues (e.g., collagens and elastin) within the wound and surrounding normal tissues. This may yield useful information about the spatial orientation and organization of connective tissue fibers associated with wound remodeling during healing [Yasui et al., (2004) Appl. Opt. 43: 2861-2867].

Figure 12:
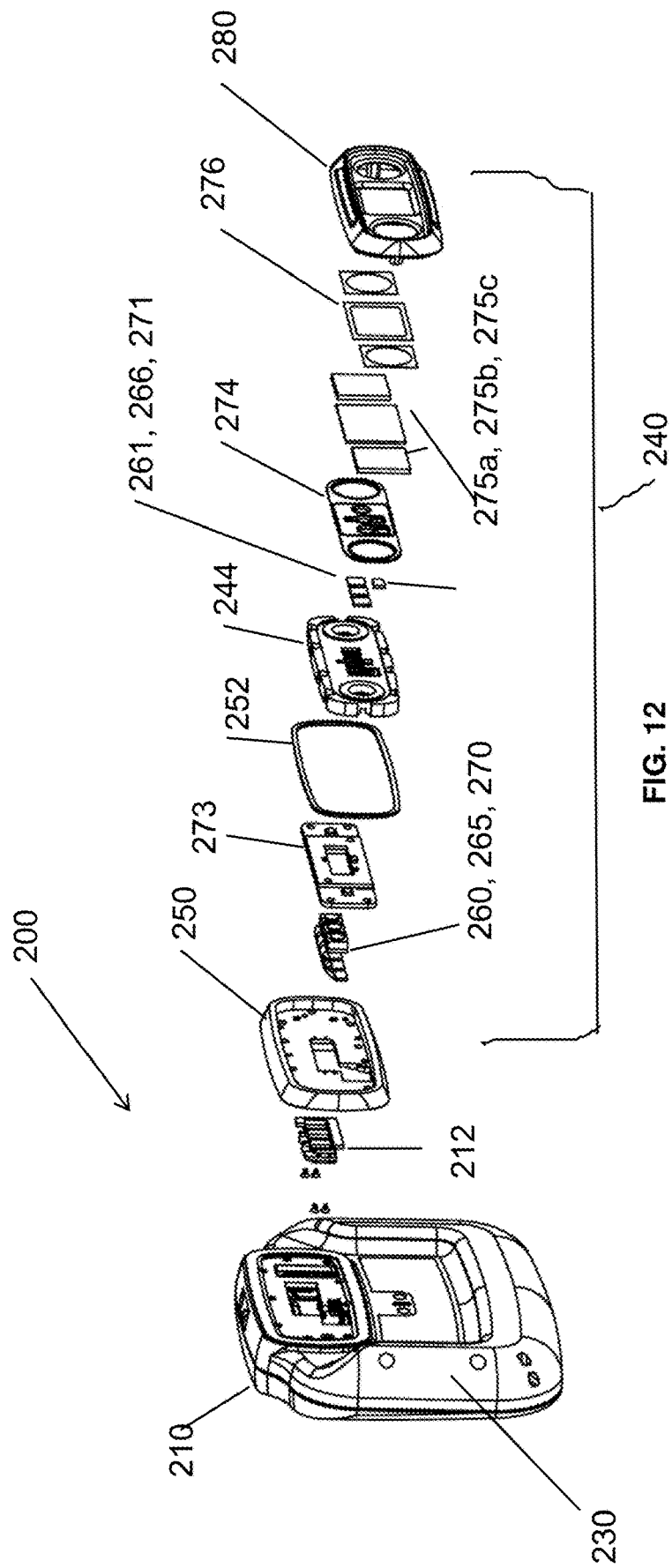
FIG. 12 is an exploded view of an example embodiment of an optical housing of an imaging device in accordance with one aspect of the present disclosure.

In one example embodiment, shown in FIG. 12, the imaging device 200 includes three camera sensors 260, 265, 270 and each sensor includes a fixed filter 261, 266, 271. For example, first and second white light sensors may be provided, each configured to receive visible light signals via a dedicated filter fixed to the respective sensor. Additionally, a sensor for fluorescent imaging may be configured to allow various desirable emission wavelengths to pass through to the fluorescent camera sensor. As previously discussed, different optical housing portions may contain different configurations of sensors, filters, and light sources which together are configured to create images of specific characteristics of a target.

FIG. 12 shows an exploded view of the optical housing 240 of imaging device 200. As shown in FIG. 12, base body portion 210 may include a heat sink 212 positioned behind heat sink 250 of the optical housing 240. Optical housing 240 may further include three camera sensors 260, 265, 270, a printed circuit board (PCB) 273, an outer heat sink gasket 252, a camera shroud 244, three optical filters 261, 266, 271, a light diffuser 253 for the white light source, an inner gasket/filter retainer 274, windows 275a, 275b, 275c, adhesive tape 276 (or other means for fixing the windows), and a lens assembly tip 280, which may include a feature to permit attachment of accessories.

As will be understood by those of skill in the art, the arrangement of the components in the optical housing of the imaging device may take on many configurations. Such configurations may be driven by size of the device, the footprint of the device, and the number of components used. However, when arranging the components, functional factors should also be considered. For example, issues such as light leakage from light sources of the device and/or an ambient light entering the optical housing may interfere with proper or optimal operation of the device, and may for example cause a less desirable output, such as image artifacts. The arrangement illustrated in FIG. 12 is an arrangement in which camera sensors are isolated so as to prevent light leakage from light sources and ambient light.

Figure 13:
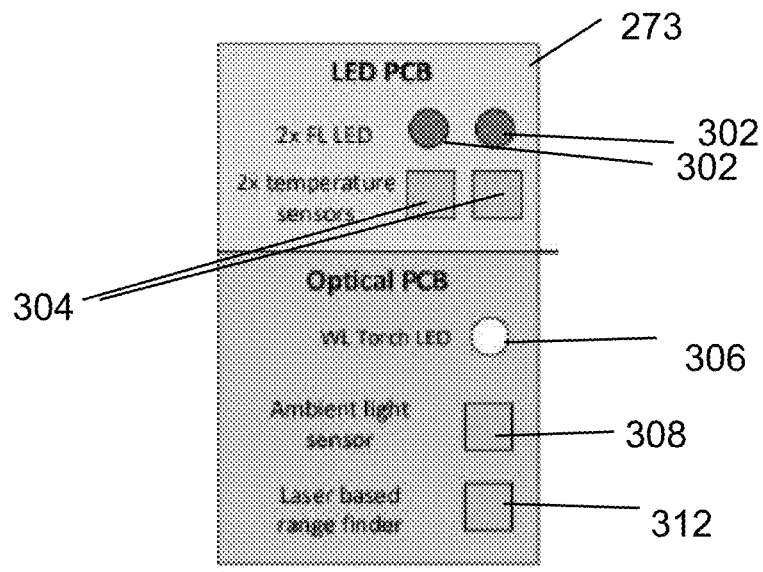
FIG. 13 is an example embodiment of a printed circuit board for use in an imaging device in accordance with one aspect of the present disclosure.

An example PCB 273 is shown in FIG. 13. As illustrated, the PCB may include an excitation light source 302, such as for example two fluorescent LEDs, for example violet/blue LEDs having a wavelength of between about 400 nm-about 450 nm, and in one example, having a wavelength of about 405 nm. Additional LEDs having the same wavelength may be provided or only one LED may be used. Additionally, it is contemplated that additional excitation light sources having different wavelengths may be provided. PCB 273 may also include two temperature sensors 304, a white light or torch LED 306 to provide white light for white light imaging, an ambient light sensor 308, and a range finder 312, which may be, for example, a laser-based range finder.

When the device 100 or 200 is held above a target tissue surface (e.g., a wound) to be imaged, the illuminating light sources may shine a narrow-bandwidth or broad-bandwidth violet/blue wavelength or other wavelength or wavelength band of light onto the tissue/wound surface thereby producing a flat and homogeneous field of light within the region-of-interest. The light also illuminates or excites the tissue down to a certain shallow depth. This excitation/illumination light interacts with the normal and diseased tissues and may cause an optical signal (e.g., absorption, fluorescence and/or reflectance) to be generated within the target tissue, which is subsequently captured by one of the camera sensors.

By changing the excitation and emission wavelengths accordingly, the imaging device 100, 200 may interrogate tissue components of the target (e.g., connective tissues and bacteria in a wound) at the surface and at certain depths within the target tissue (e.g., a wound). For example, by changing from violet/blue (~400-500 nm) to green (~500-540 nm) wavelength light, excitation of deeper tissue/bacterial fluorescent sources may be achieved, for example in a wound. Similarly, by detecting longer wavelengths, fluorescence emission from tissue and/or bacterial sources deeper in the tissue may be detected at the tissue surface. For wound assessment, the ability to interrogate surface and/or subsurface fluorescence may be useful, for example in detection and potential identification of bacterial contamination, colonization, critical colonization and/or infection, which may occur at the surface as well as at depth within a wound (e.g., in chronic non-healing wounds).

The handheld imaging device 100, 200 also includes an imaging lens and an image sensor in the optical housing portion 140, 240 of the device. The imaging lens or lens assembly may be configured to focus the filtered autofluorescence emissions and fluorescence emissions on the image sensor. A wide-angle imaging lens or a fish-eye imaging lens are examples of suitable lenses. A wide-angle lens may provide a view of 180 degrees. The lens may also provide optical magnification. A very high resolution is desirable for the imaging device, such that it is possible to make distinctions between very small groups of cells. The image sensor is configured to detect the filtered autofluorescence emissions of tissue cells and fluorescence emissions of the induced porphyrins in tissue cells. The image sensor may have 4K video capability as well as autofocus and optical or digital zoom capabilities. CCD or CMOS imaging sensors may be used. In one example, a CMOS sensor combined with a filter may be used, i.e., a hyperspectral image sensor, such as those sold by Ximea Company.

Example filters include a visible light filter (https://www.ximea.com/en/products/hyperspectral-cameras-based-on-usb3-xispec/mq022hg-im-sm4x4-vis) and an IR filter (https://www.ximea.com/en/products/hyperspectral-cameras-based-on-usb3-xispec/mq022hg-im-sm5×5-nir). The handheld device 100, 200 also may contain a processor configured to receive the detected emissions and to output data regarding the detected filtered autofluorescence and/or exogenous fluorescence emissions. The processor may have the ability to run simultaneous programs seamlessly (including but not limited to, wireless signal monitoring, battery monitoring and control, temperature monitoring, image acceptance/compression, and button press monitoring). The processor interfaces with internal storage, physical controls such as buttons, optics, and the wireless module. The processor also has the ability to read analog signals.

The imaging device 100, 200 may also include a wireless module and be configured for completely wireless operation. It may utilize a high throughput wireless signal and have the ability to transmit high definition video with minimal latency. The device may be both Wi-Fi and Bluetooth enabled—Wi-Fi for data transmission, Bluetooth for quick connection. The device may utilize a 5 GHz wireless transmission band operation for isolation from other devices. Further, the device may be capable of running as soft access point, which eliminates the need for a connection to the internet and keeps the device and module connected in isolation from other devices which is relevant to patient data security. The device may be configured for wireless charging and include inductive charging coils. Additionally or alternatively, the device may include a port configured to receive a charging connection.

Figure 14A:
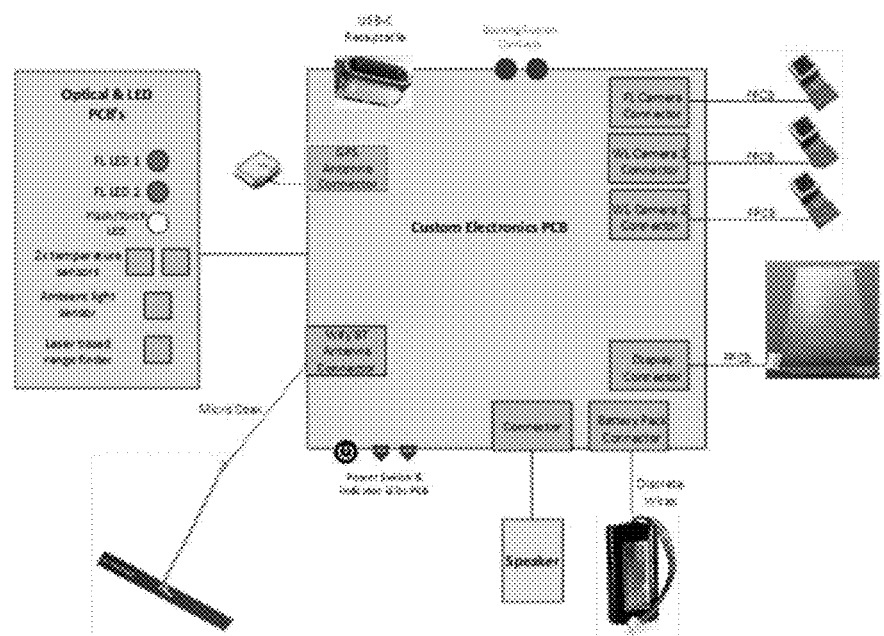
FIGS. 14A and 14B show example hardware block diagrams for use in imaging devices of the present disclosure.
Figure 14B:
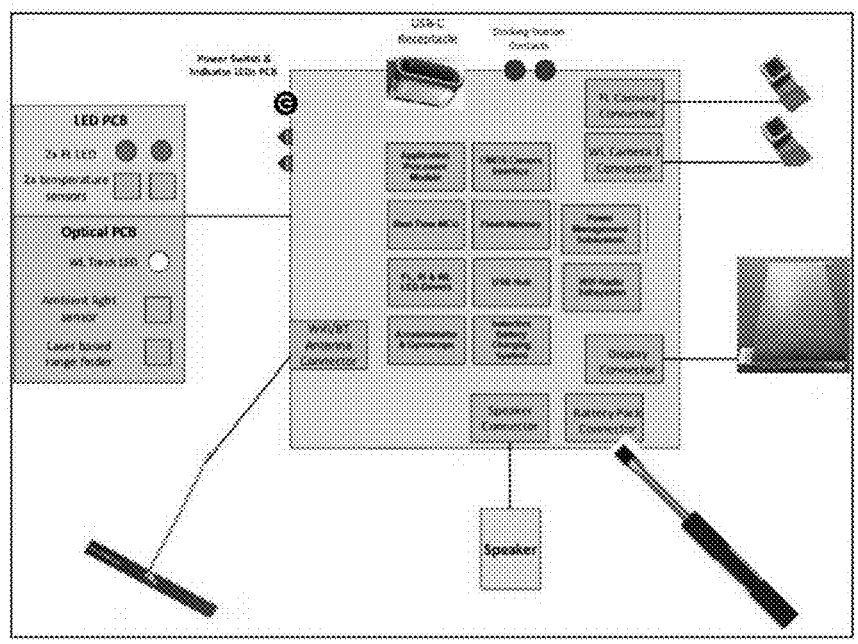

FIGS. 14A and 14B illustrate alternative embodiments of a hardware block diagram for the devices 100, 200. FIGS. 14A and 14B illustrate example block diagrams showing the various components of a handheld imaging device 100, 200 according to example embodiments of the present disclosure.

The components of the handheld imaging device 100, 200, may be grouped in an optical PCB and an electronics system. In the embodiment of FIG. 14B, the optical PCB includes 4 fluorescent wavelength LEDs, 2 infrared LEDs, and two white light LEDs. The optical PCB further includes an ambient light sensor, a laser range finder, and a temperature sensor.

The optical PCB is operably coupled with the electronics system 302. The electronics system can include, for example and without limitation, electronic control components such as an application processor module, a real time microcontroller unit (MCU), and a power management subsystem. The electronics system can further include components and systems that interface with other electronic components of the handheld imaging device. For example, the electronics system can include a CMOS camera interface and motor drive electronics for the optical filter system. The electronics system can also include connectors for the fluorescent and white light cameras, respectively, to facilitate switching between the fluorescent and white light imaging modes discussed herein. Although only two cameras, a white light camera and a fluorescent camera are shown in FIG. 14B, the present disclosure contemplates the use of additional cameras, particularly white light cameras. For example, the example block diagram of FIG. 14A discloses the presence of three cameras, two white light cameras and one fluorescent camera. The addition of further cameras is within the scope of the present disclosure.

Other supporting electronic systems and components of the electronics system can include memory, such as a flash memory device, a rechargeable battery such as a lithium-ion battery, and an inductive battery charging system. Some components of the electronics system can include communications components, such as Wi-Fi and/or Bluetooth radio subsystem, and spatial orientation components such as one or more of magnetometers, accelerometers, and gyroscopes.

The electronics system can include various user controls, such as a power switch, system status LEDs, charging status LEDs, a picture capture switch, video capture switch, and imaging mode switch. The various user controls can interface with the other components of the electronics system through a user interface module that provides signals to and from the user controls.

Other components in the electronic system can include drivers for the fluorescent, infrared, and white light LEDs, a USB hub for uplink or downlink data signals and/or power supply from an external computer system to which the electronic system can be connected through the USB hub, such as a workstation or other computer. The electronics system can also include one or more devices that provide feedback to a user, such as, without limitation, a speaker. Other feedback devices could include various auditory and visual indicators, haptic feedback devices, displays, and other devices.

The modular handheld imaging device 100, 200 of the present application may be used with various accessories. For example, the device 100, 200 may be used with a drape configured to darken the area around the target being imaged by blocking or reducing ambient light around the target. The drape may include an adapter configured to fit on a patient facing side of the optical housing and configured to isolate and/or separate the optics of the optical housing from ambient light by forming a barrier between them. Examples of the types of drapes to be used with this device may be found, for example, in U.S. Provisional Patent application No. 62/669,009 filed May 9, 2018 and entitled "Darkening Drape, Packaging for Drape, Method of Use and Method for Deploying Same," International Patent Application PCT/CA2019/000061 filed May 9, 2019 and entitled "IMAGING DRAPES, PACKAGING FOR DRAPES, METHODS OF USE OF IMAGING DRAPES, AND METHODS FOR DEPLOYING DRAPE," U.S. Design Pat. Application No. 29/647,110, filed May 9, 2018 and entitled "Darkening Drape," and Design Application No. 29/676,893, filed Jan. 15, 2019 and entitled "Adaptor for Supporting a Darkening Drape," the entire content of each of which is incorporated herein by reference.

Figure 15A:
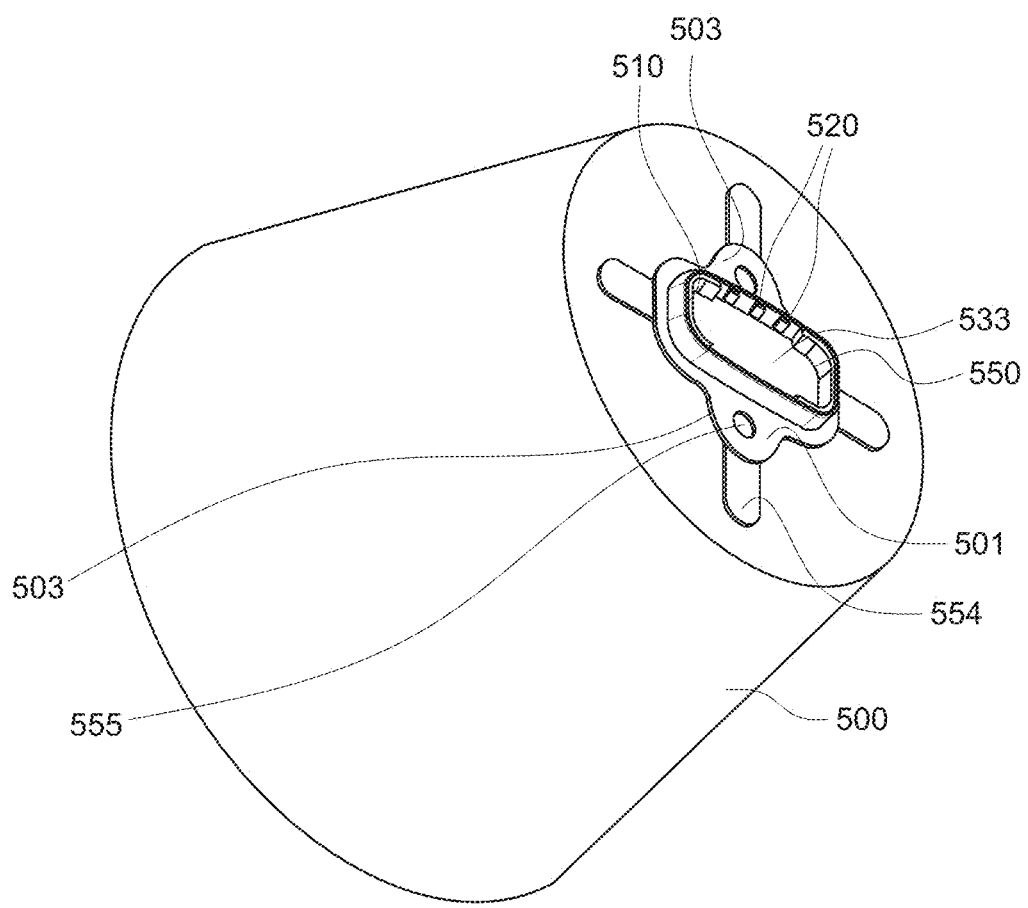
FIGS. 15A-15F show an example embodiment of a drape unconnected to (FIGS. 15A-15C) and connected to (FIGS. 15D-15E) a portable, handheld imaging device in accordance with the present disclosure.
Figure 15B:
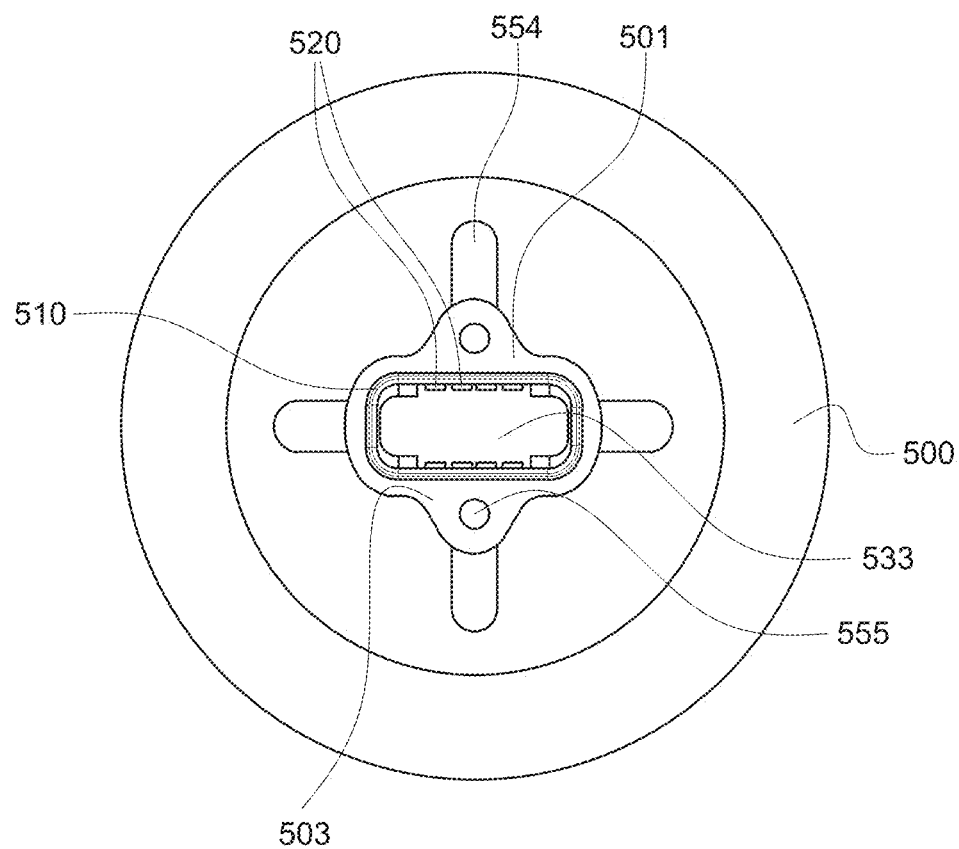
Figure 15C:
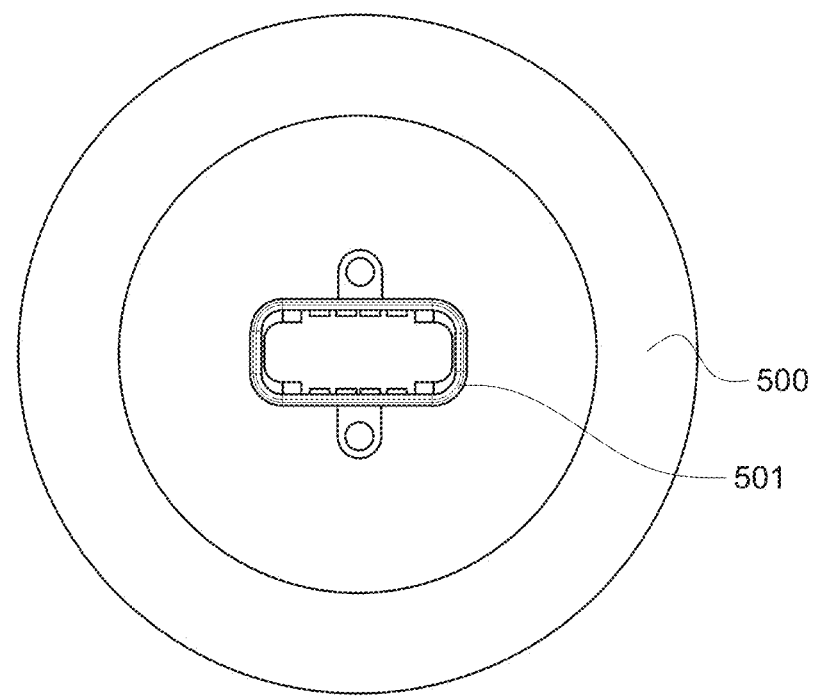

In accordance with one example embodiment, a darkening drape 500 is disclosed. FIGS. 15A-15C show an example embodiment of an imaging drape 500. The imaging drape 500 is shown connected to an imaging device such as the imaging devices 100, 200 previously discussed herein in FIGS. 15D-15F. The drape 500 may be used in conjunction with any of the imaging devices disclosed herein. Drape 500 includes connecting element 501. In the example embodiment, connecting element 501 includes a ridge 510 that is used to form a press-fit or snap-fit connection with the imaging device 100, 200. A projection on the imaging device 100, 200 (as discussed below) may engage with ridge 510 to provide the press-fit or snap-fit connection. Additionally, one or more protrusions 520 may be configured to engage with the projection on the imaging device 100, 200 to grip the imaging device 100, 200 and better secure it to the drape. In some embodiments, protrusions 520 are teeth-like members that engage with the projection on the imaging device. When an imaging device is properly aligned and pressed down into connecting element, protrusions 520 clip into the projection on the imaging device in order to provide the snap-fit connection.

Connecting element 501 may also include end cup members to 550 to help facilitate the snap-fit connection between connecting element 501 and the imaging device. As shown in FIG. 15A, end cup members 550 may be smooth members disposed at either end of opening 533, which is formed within connecting element 501. End cup members 550 may provide guidance to center/position the imaging head/optical head of the imaging device that is snap-fitted into connecting element 501.

FIG. 15A shows opening 533 as having a rectangular shape with protrusions 520 disposed on the longer sides of the rectangular shape and end cup members 550 disposed on the shorter sides of the rectangular shape. However, it is also contemplated that protrusions 520 may be disposed on the shorter sides of the rectangular shape and that end cup members 550 may be disposed on the longer sides of the rectangular shape. Although FIG. 15A shows two end cup members 550, only one end cup member 550 may be used on one side of opening 533. Furthermore, in some embodiments, connecting element 501 may not include end cup members 550. In this embodiment, protrusions 520 may be disposed around a majority or the entire perimeter of opening 533 on connecting element 501. Connecting element 501 may be formed of injection molded plastic, as discussed above.

FIG. 15A shows a top, perspective view of connecting element 501 secured to a drape. FIG. 15B shows a top view of connecting element 501 and an exterior view of the drape, and FIG. 15C shows a bottom view of connecting element 500 and a view of the portable imaging environment formed by an interior of the drape.

Connecting element 501 may also include a top, planar surface 503, one-way valves, such as a flap valves 555, and projections 554. As shown, projections 554 are disposed on a top surface of connecting element 501. Therefore, projections 554 are viewable from the top view of FIG. 15B but are not viewable from the interior of the drape in the view of FIG. 15C. Projections 554 help to hold the drape material out of the imaging field of view.

In the embodiment of FIGS. 15A-15F, connecting element 501 may be formed of an injection molded plastic, such as polyethylene. Thus, connecting element 501 may be a relatively stiff member. In some embodiments, connecting element 501 has a thickness of about 1.8 mm. Projections 554 may be formed of the same material as the remainder of connecting element 501 but may be less stiff than the remainder of connecting element 501. Thus, projections 554 may be thinner than the remainder of connecting element 501. The material of the drape body may be formed of the same material as connecting element 501 but may not be ejection molded so that the material of the drape body is less stiff than connecting element 501 (including projections 554). In some embodiments, the material of the drape body is also thinner than connecting element 501 (including projections 554). The drape body may be formed of a soft material that is welded to the relatively stiffer material of connecting element 501. This may lower manufacturing costs by allowing flap valves 555 to be integrated into the drape by being formed by the material of the drape body.

Connecting element 501 also includes opening 533 in order to provide, from the imaging device 100, 200, FL and/or white-light imaging within the interior environment of the drape. In the embodiment of FIGS. 15A-15C, opening 533 is substantially rectangular in shape. However, it is further contemplated that other shapes may be used.

Figure 15D:
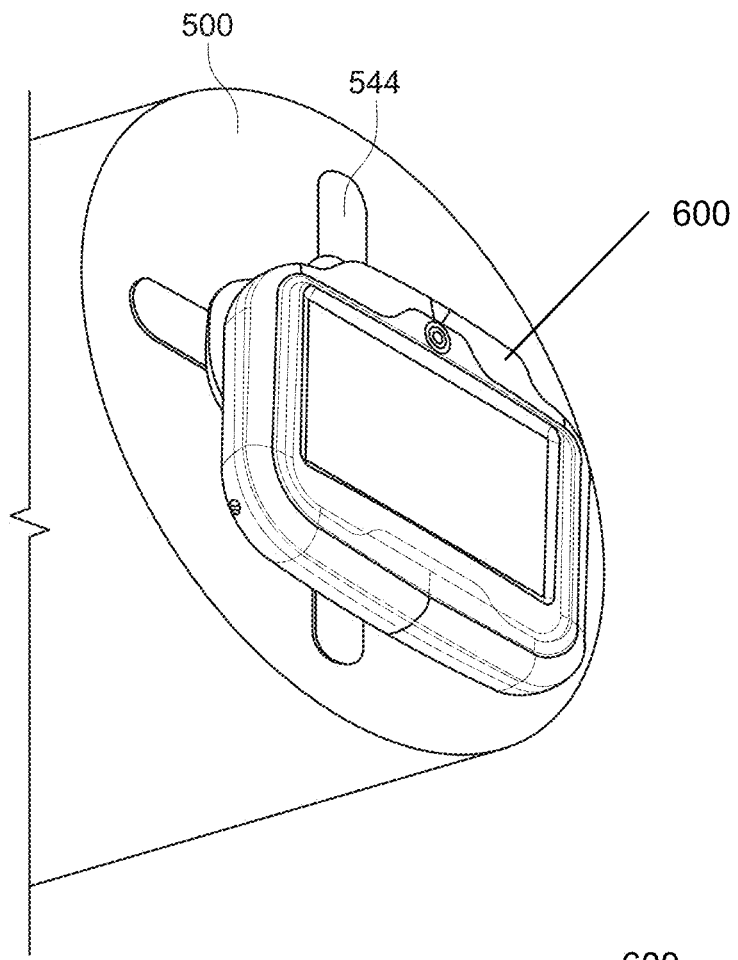
Figure 15E:
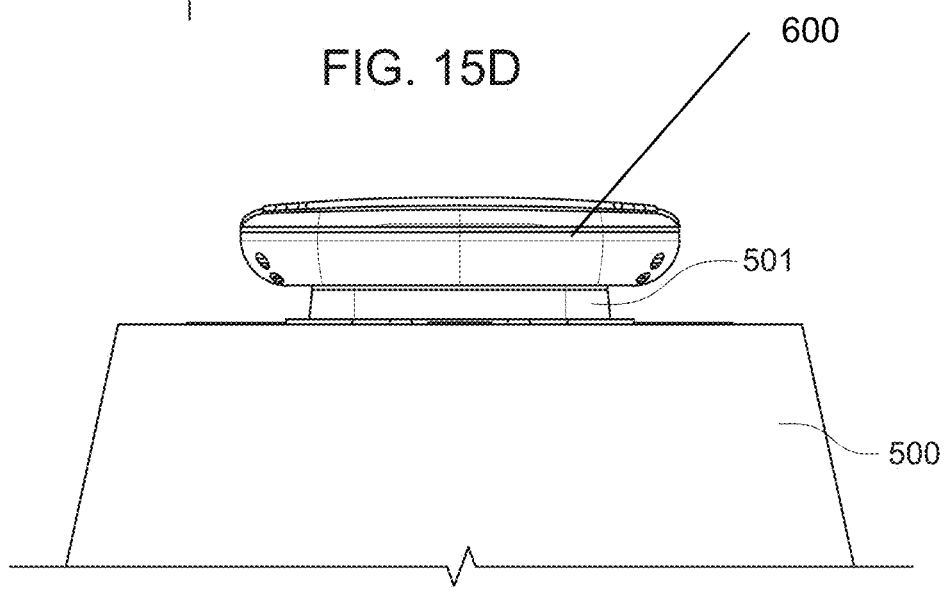
Figure 15F:
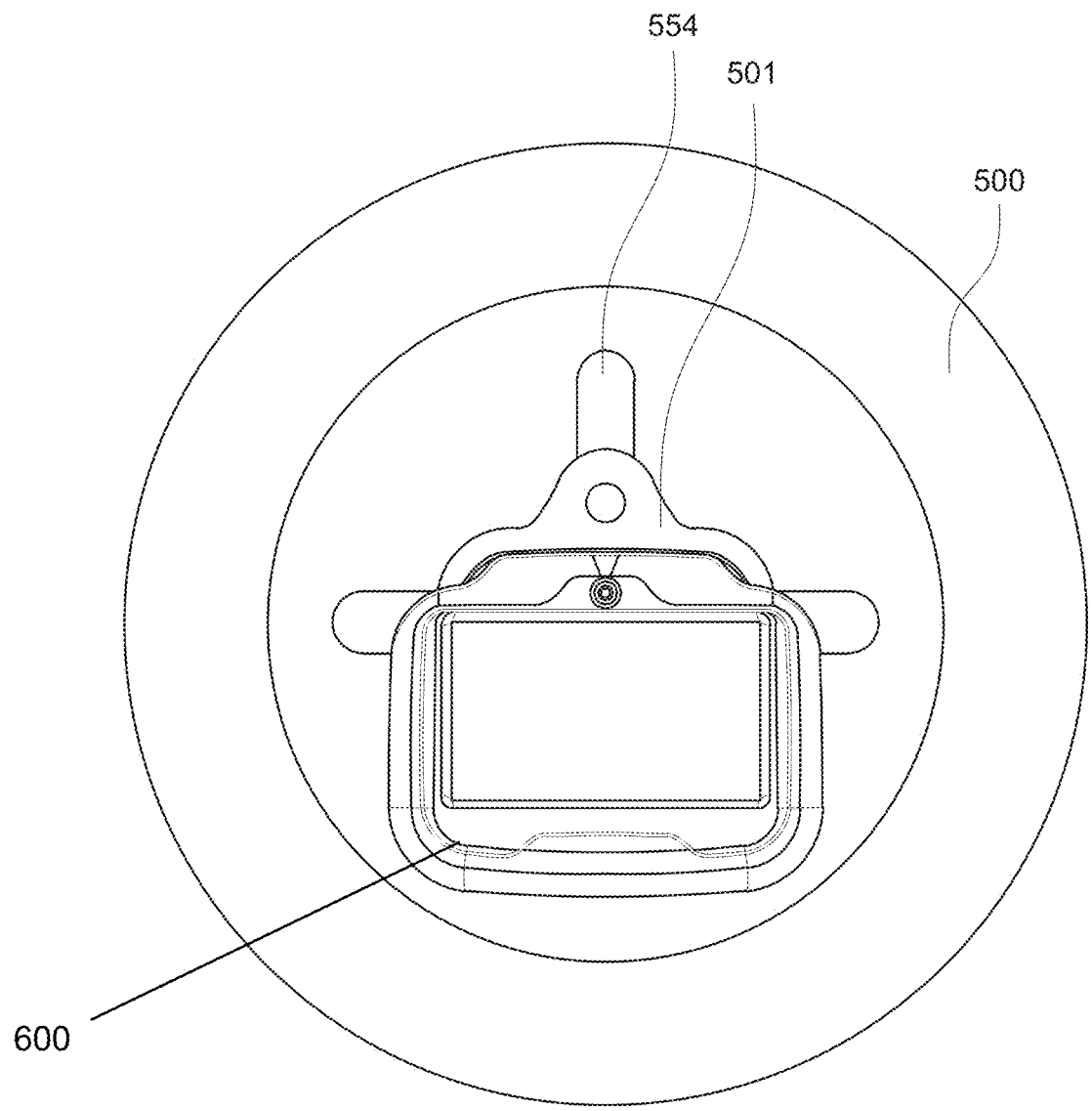

FIGS. 15D-15F show an example of an imaging device 600 secured to connecting element 501 of the drape shown in FIGS. 15A-15C. Imaging device 600 may be configured as described with regard to devices 100, 200 discussed above. The imaging device 600 is securely fastened to connecting element 501 through a snap-fit connection that prevents/reduces any ambient light from entering the interior of the drape through the top of the drape. A projection 670 on imaging device 600 may engage with protrusions 520 and ridge 510 on connecting element 501 to provide the snap-fit connection, as discussed above.

Figure 15G:
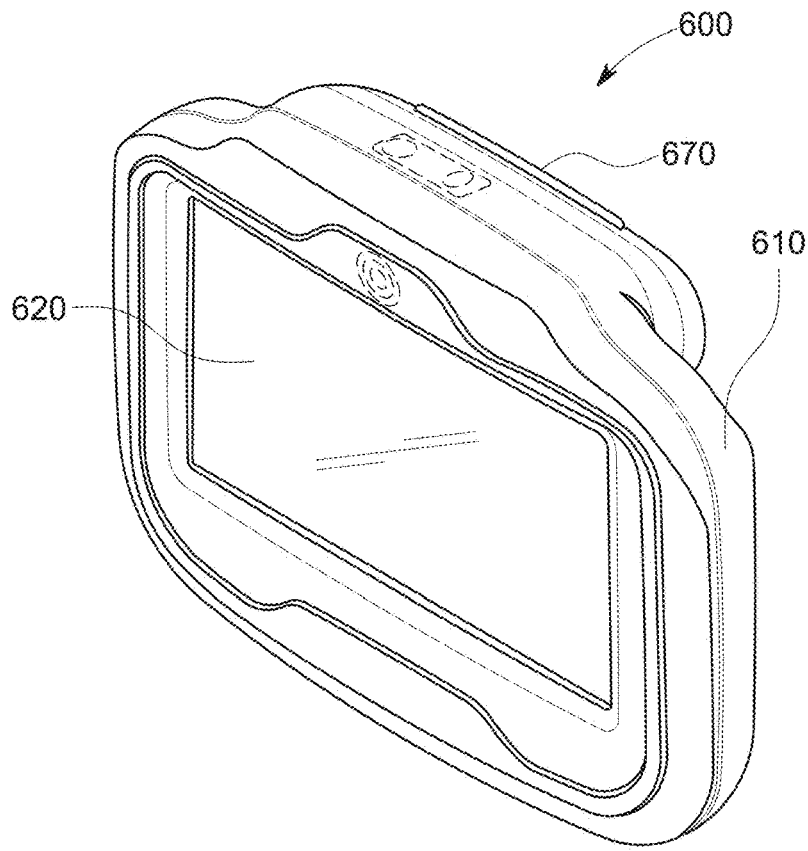
FIGS. 15G-15H show the example portable, handheld imaging device connected to the drape of FIGS. 15D-15F in accordance with the present disclosure.
Figure 15H:
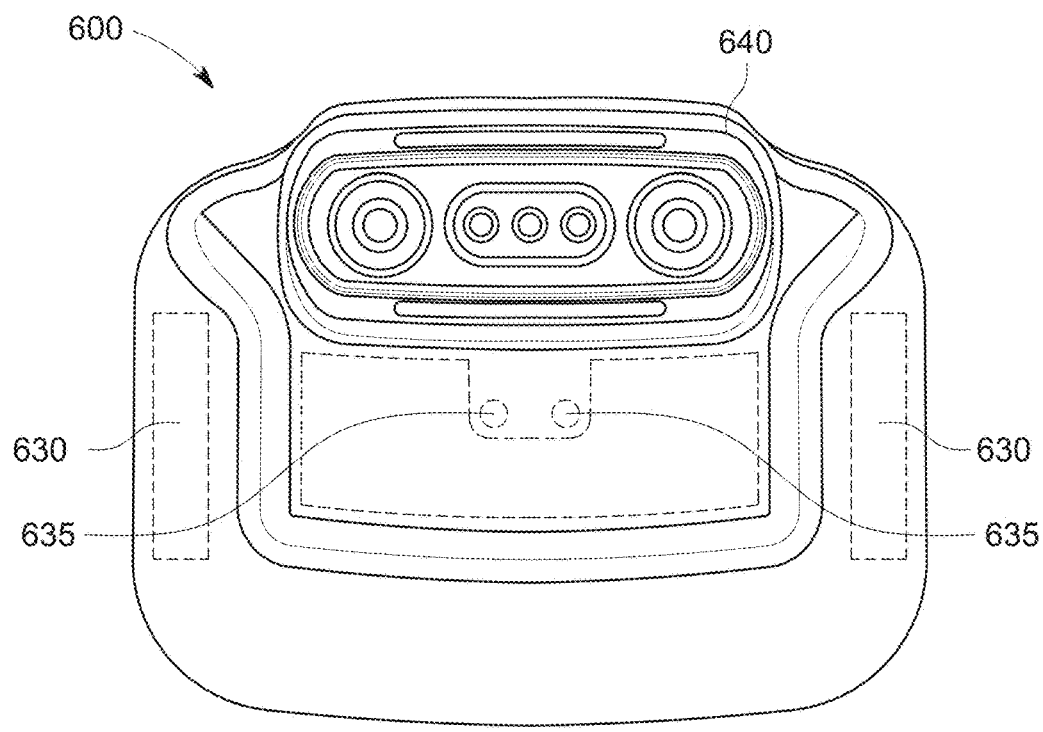

An example embodiment of a modular handheld imaging device 600 is shown in FIGS. 15G and 15H. Imaging device 600 includes a base body portion 610 with a generally square or rectangular shape. A front, or user-facing side 615 of the base body portion 610 includes a display screen 620 for displaying images and videos captured by the device. Projection 670 projects outward from optical head/optical housing 640 although, alternatively, it may be positioned on base body portion 610. Although FIG. 15G shows projection 670 as disposed on a top portion of base body portion 610, it is also contemplated that projection 670 may be disposed on other sides of base body portion 610, depending on the location of protrusions 520 on connecting element 501.

Although depicted as square or rectangular, imaging device 600 may take on any shape that will reasonably support a display screen such as a touchscreen. In addition to disclosing images captured by the imaging device 600, the display screen also operates as a user interface, allowing the user to control functions of the device via touchscreen input.

Positioned on an opposite side of the device, a patient-facing side 625 of the device, may be handhold areas 630 configured to facilitate a user holding the device during imaging. The patient facing-side of the device may also incorporate contacts 635 for wireless charging of the device.

In accordance with one aspect of the present disclosure, the patient-facing side of device 600 also includes an optical housing 640. Optical housing 640 may be detachable from base body portion 610. Optical housing portion 640 is illustrated as a rectangular housing configured to be received in the opening of the connecting element on the drape.

The optical housing 640 may take on different configurations. For example, as shown in FIG. 15H, the optical housing portion 640 has a generally flat, oblong shape. Optical components, for FL and/or white light imaging, are arranged in a generally linear manner across a width of the optical housing. The optical components are described in greater detail above.

Figure 16A:
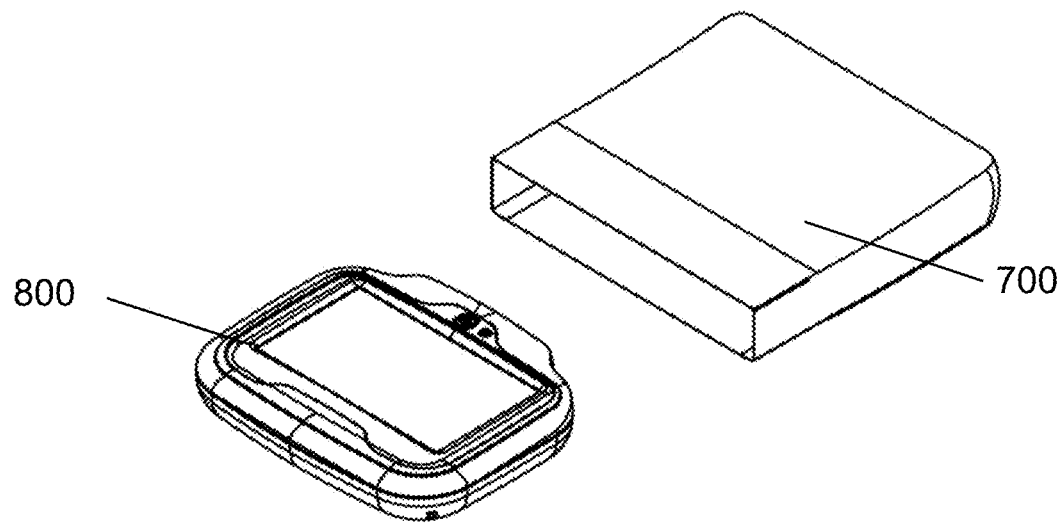
FIGS. 16A-16C show an example embodiment of a sterile drape for use with an imaging device (FIGS. 16A-16B) and the sterile drape on the imaging device as it is connected to a darkening drape/imaging drape (FIG. 16C) in accordance with the present disclosure.
Figure 16B:
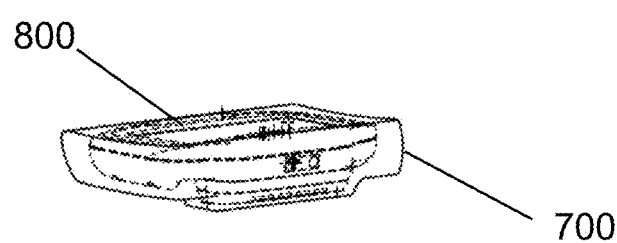
Figure 16B:
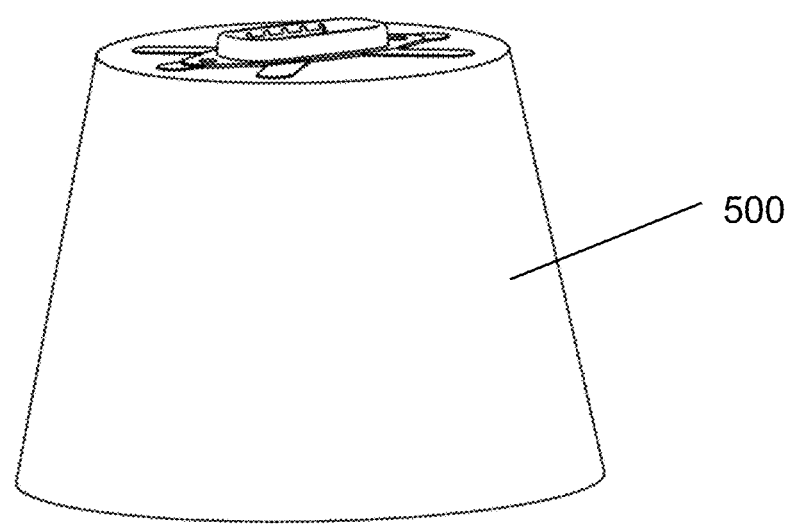
Figure 16C:
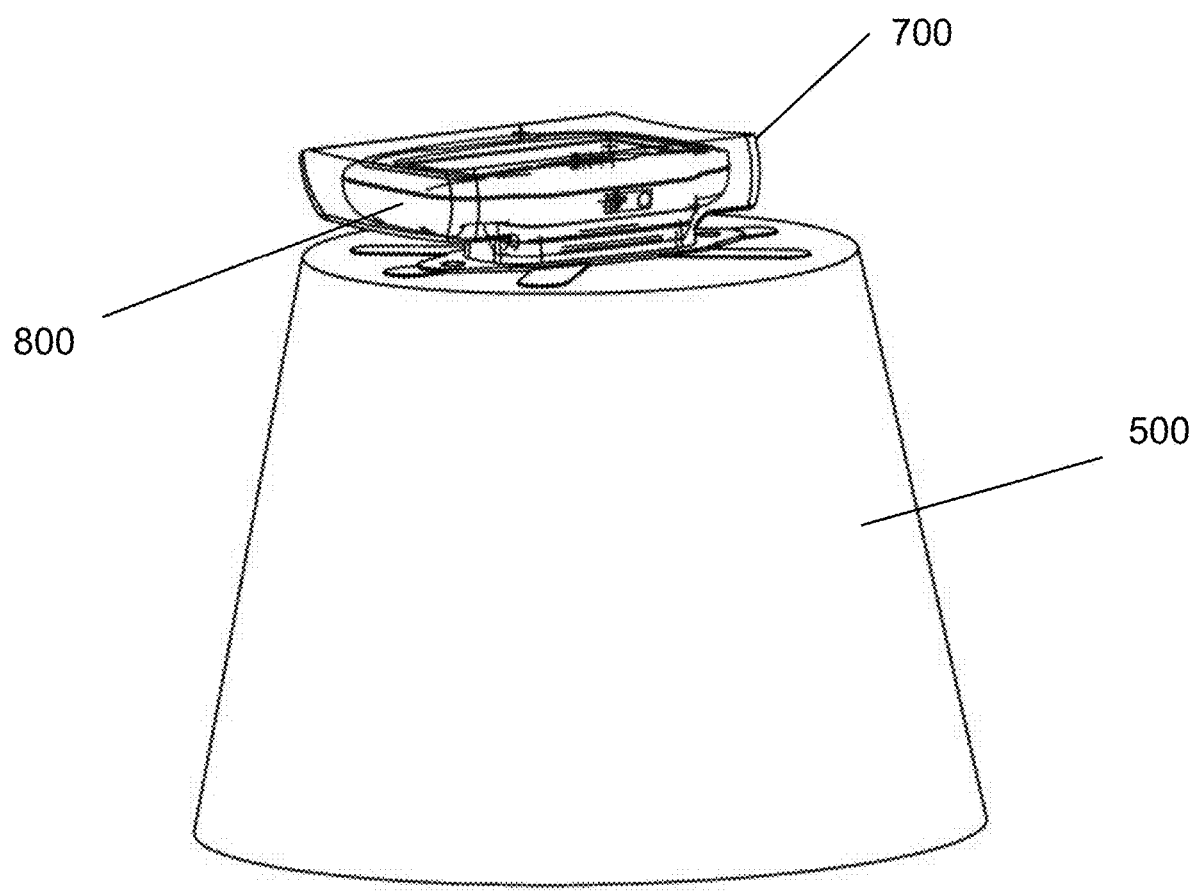

In accordance with another aspect of the present disclosure, the imaging devices 100, 200, 600 of the present disclosure may be used with a sterile drape. The sterile drape configured to form a sterile barrier between the imaging device 100, 200, 600 and an environment in which the imaging device is used. An example embodiment of a sterile drape for use with the imaging device of the present disclosure is illustrated in FIGS. 16A-16C. As shown in FIG. 16A, a sterile drape 700 may be configured to receive a body of an imaging device 800. When the sterile drape is positioned on the imaging device 800, the imaging device may be engaged with a darkening drape 500, as discussed above with regard to FIGS. 15A-15H and as shown in FIGS. 16B and 16C.

The optical housings may be configured such that a single adapter will fit all optical housings to attach a darkening drape. Alternatively, a separate adaptor may be provided to engage each optical housing.

In accordance with one aspect of the present disclosure, the modular handheld device may be used to obtain three-dimensional fluorescent images of the target. Systems for and methods of obtaining such three-dimensional images are disclosed in U.S. Provisional Application No. 62/793,837 filed Jan. 17, 2019 and entitled "Systems Methods, and Devices for Three-Dimensional Imaging, Measurement, and Display of Wounds and Tissue Specimens," the entire content of which is incorporated herein by reference.

Other uses for the device may include:
Clinically- and research-based imaging of small and large (e.g., veterinary) animals.
Detection and monitoring of contamination (e.g., bacterial contamination) in food/animal product preparation in the meat, poultry, dairy, fish, agricultural industries.
Detection of 'surface contamination' (e.g., bacterial or biological contamination) in public (e.g., health care) and private settings.
Multi-spectral imaging and detection of cancers in human and/or veterinary patients.
As a research tool for multi-spectral imaging and monitoring of cancers in experimental animal models of human diseases (e.g., wound and cancers).
Forensic detection, for example of latent finger prints and biological fluids on non-biological surfaces.
Imaging and monitoring of dental plaques, carries and cancers in the oral cavity.
Imaging and monitoring device in clinical microbiology laboratories.
Testing anti-bacterial (e.g., antibiotic), disinfectant agents.

The device may generally comprise: i) one or more excitation/illumination light sources and ii) one or more image sensors which may be combined with one or more optical emission filters, or spectral filtering mechanisms. The device may have a view/control screen (e.g., a touch-sensitive screen), image capture and zoom controls. The device may also have: iii) a wired and/or wireless data transfer port/module, iv) an electrical power source and power/control switches.

The device can include software allowing a user to control the device, including control of imaging parameters, visualization of images, storage of image data and user information, transfer of images and/or associated data, and/or relevant image analysis (e.g., diagnostic algorithms). The device can further include software for measuring the imaged target, calculating quantities of various items found in the imaged target. For example, if the target is a wound, the device can include software configured to calculate wound size, wound depth, wound perimeter, wound area, wound volume, identify various types of tissues within the wound (collagen, elastic, vasculature) and the percentages of each within the wound. Further, the device can determine an amount or quantity of bacteria in the wound, the bacterial load, distinguish between various types of bacteria within the load and identify relative percentages. Examples of suitable software and methods are described, for example, in U.S. Provisional Patent Application No. 62/625,611, filed Feb. 2, 2019 and entitled "Wound Imaging and Analysis" and International patent application no. PCT/CA2019/000002, filed Jan. 15, 2019 and entitled "Wound Imaging and Analysis," the entire content of each of which is incorporated by reference herein.

The device may be configured to co-register white light images, fluorescent images, thermal images and other images of a target. The device may be configured to create three-dimensional maps of a target. The device may be configured to enhance color distinctions between different tissue types identified in an image. The device may be configured to determine tissue classification of the target based on different colors or image features captured in the fluorescent image. The device may be configured to delineate between diseased and healthy tissues therein providing a map for users to selectively remove diseased tissues while sparing surrounding healthy tissues is a targeted manner.

Various types of filters, power sources, light sources, excitation light sources, image sensors, and charging configurations may be present in the presently disclosed device. Examples of such components are described, for example, in U.S. Pat. No. 9,042,967, which is a national stage application of PCT/CA2009/000680, filed internationally on May 20, 2009, which claims benefit to U.S. Provisional Application No. 61/054,780, filed May 20, 2008, the entire content of each of which is incorporated by reference herein. Additional components are disclosed in U.S. Provisional Application No. 62/625,983 (filed Feb. 3, 2018) entitled "Devices, Systems, and Methods for Tumor Visualization and Removal" and U.S. Provisional Application No. 62/625,967 (filed Feb. 2, 2018) entitled "Devices, Systems, and Methods for Tumor Visualization and Removal," the entire contents of each of which are incorporated by reference herein. Additional components are disclosed in U.S. Provisional Patent Application No. 62/793,764, filed Jan. 17, 2019 and entitled "Multimodal System for Visualization of Disease," and U.S. Provisional Patent Application No. 62/857,155, filed Jun. 4, 2019 and entitled "DEVICES, SYSTEMS, AND METHODS FOR TUMOR VISUALIZATION," the entire contents of each of which are incorporated herein by reference.

The imaging systems and methods disclosed herein may rely on tissue autofluorescence and bacterial autofluorescence, as well as autofluorescence of other targeted materials. Additionally or alternatively, the present application contemplates the use of exogenous contrast agents which may be applied topically, ingested, or otherwise applied. Examples of such agents for imaging a target are disclosed, for example, in U.S. Pat. No. 9,042,967, which is a national stage application of PCT/CA2009/000680, filed internationally on May 20, 2009, which claims benefit to U.S. Provisional Application No. 61/054,780, filed May 20, 2008, the entire content of each of which is incorporated by reference herein. Additional components are disclosed in U.S. Provisional Application No. 62/625,983 (filed Feb. 3, 2018) entitled "Devices, Systems, and Methods for Tumor Visualization and Removal" and U.S. Provisional Application No. 62/625,967 (filed Feb. 2, 2018) entitled "Devices, Systems, and Methods for Tumor Visualization and Removal," the entire contents of each of which are incorporated by reference herein. Additional components are disclosed in U.S. Provisional Patent Application No. 62/793,764 filed January 17, 2019 and entitled "Multimodal System for Visualization of Disease," and U.S. Provisional Patent Application No. 62/857,155, filed Jun. 4, 2019 and entitled "DEVICES, SYSTEMS, AND METHODS FOR TUMOR VISUALIZATION," the entire contents of each of which are incorporated herein by reference.

The device interface ports may support both wired (e.g., USB) or wireless (e.g., Bluetooth, WiFi, and similar modalities) data transfer or 3$^{rd}$ party add-on modules to a variety of external devices, such as: a head-mounted display, an external printer, a tablet computer, laptop computer, personal desk top computer, a wireless device to permit transfer of imaging data to a remote site/other device, a global positioning system (GPS) device, a device allowing the use of extra memory, and a microphone.

The device may be used to guide debridement of wounds, to identify types of bacteria to assist in determination of appropriate treatments/drugs/antibiotics.

The device may also be attached to a mounting mechanism (e.g., a tripod or stand) for use as a relatively stationary optical imaging device for white light, fluorescence and reflectance imaging of objects, materials, and surfaces (e.g., a body). This may allow the device to be used on a desk or table or for 'assembly line' imaging of objects, materials and surfaces. In some embodiments, the mounting mechanism may be mobile.

Other features of this device may include the capability of digital image and video recording, with audio, methods for documentation (e.g., with image storage and analysis software), and wired or wireless data transmission for remote telemedicine/E-health needs.

In addition to providing detecting of bacterial strains, the device may be used for differentiating the presence and/or location of different bacterial strains (e.g., *Staphylococcus aureus* or *Pseudomonas aeruginosa*), for example in wounds and surrounding tissues. This may be based on the different autofluorescence emission signatures of different bacterial strains, including those within the 490-550 nm and 610-640 nm emission wavelength bands when excited by violet/blue light, such as light around 405 nm. Other combinations of wavelengths may be used to distinguish between other species on the images. This information may be used to select appropriate treatment, such as choice of antibiotic.

The device may be scanned above any wound (e.g., on the body surface) such that the excitation light may illuminate the wound area. The wound may then be inspected using the device such that the operator may view the wound in real-time, for example, via a viewer on the imaging device or via an external display device (e.g., heads-up display, a television display, a computer monitor, LCD projector or a head-mounted display). It may also be possible to transmit the images obtained from the device in real-time (e.g., via wireless communication) to a remote viewing site, for example for telemedicine purposes, or send the images directly to a printer or a computer memory storage. Imaging may be performed within the routine clinical assessment of patient with a wound.

Prior to imaging, fiduciary markers (e.g., using an indelible fluorescent ink pen) may be placed on the surface of the skin near the wound edges or perimeter. For example, four spots, each of a different fluorescent ink color from separate indelible fluorescent ink pens, which may be provided as a kit to the clinical operator, may be placed near the wound margin or boundary on the normal skin surface. These colors may be imaged by the device using the excitation light and a multispectral band filter that matches the emission wavelength of the four ink spots. Image analysis may then be performed, by co-registering the fiduciary markers for inter-image alignment. Thus, the user may not have to align the imaging device between different imaging sessions. This technique may facilitate longitudinal (i.e., over time) imaging of wounds, and the clinical operator may therefore be able to image a wound over time without need for aligning the imaging device during every image acquisition.

In addition, to aid in intensity calibration of the fluorescence images, a disposable simple fluorescent standard 'strip' may be placed into the field of view during wound imaging (e.g., by using a mild adhesive that sticks the strip to the skin temporarily). The strip may be impregnated with one or several different fluorescent dyes of varying concentrations which may produce pre-determined and calibrated fluorescence intensities when illuminated by the excitation light source, which may have single (e.g., 405 nm) or multiple fluorescence emission wavelengths or wavelength bands for image intensity calibration. The disposable strip may also have the four spots as described above (e.g., each of different diameters or sizes and each of a different fluorescent ink color with a unique black dot placed next to it) from separate indelible fluorescent ink pens. With the strip placed near the wound margin or boundary on the normal skin surface, the device may be used to take white light and fluorescence images. The strip may offer a convenient way to take multiple images over time of a given wound and then align the images using image analysis. Also, the fluorescent 'intensity calibration' strip may also contain an added linear measuring apparatus, such as a ruler of fixed length to aid in spatial distance measurements of the wounds. Such a strip may be an example of a calibration target which may be used with the device to aid in calibration or measuring of image parameters (e.g., wound size, fluorescence intensity, etc.), and other similar calibration target may be used.

It may be desirable to increase the consistency of imaging results and to reproduce the distance between the device and the wound surface, since tissue fluorescence intensity may vary slightly if the distance changes during multiple imaging sessions. Therefore, in an embodiment, the device may have rangefinder in order to determine a fixed or variable distance between the device and the wound surface.

The device may be used to take white light images of the total wound with normal surrounding normal tissues using a measuring apparatus (e.g., a ruler) placed within the imaging field of view. This may allow visual assessment of the wound and calculation/determination of quantitative parameters such as the wound area, circumference, diameter, and topographic profile. Wound healing may be assessed by planimetric measurements of the wound area at multiple time points (e.g., at clinical visits) until wound healing. The time course of wound healing may be compared to the expected healing time calculated by the multiple time point measurements of wound radius reduction using the equation R=√A/π (R, radius; A, planimetric wound area; π, constant 3.14). This quantitative information about the wound may be used to track and monitor changes in the wound appearance over time, in order to evaluate and determine the degree of wound healing caused by natural means or by any therapeutic intervention. This data may be stored electronically in the health record of the patient for future reference. White light imaging may be performed during the initial clinical assessment of the patient by the operator.

The device may be designed to detect all or a majority of tissue autofluorescence (AF). For example, using a multispectral band filter, the device may image tissue autofluorescence emanating from the following tissue biomolecules, as well as blood-associated optical absorption, for example under 405 nm excitation: collagen (Types I, II, III, IV, V and others) which appear green, elastin which appears greenish-yellow-orange, reduced nicotinamide adenine dinucleotide (NADH), flavin adenine dinucleotide (FAD), which emit a blue-green autofluorescence signal, and bacteria/microorganisms, most of which appear to have a broad (e.g., green and red) autofluorescence emission.

Image analysis may include calculating a ratio of red-to-green AF in the image. Intensity calculations may be obtained from regions of interest within the wound images. Pseudo-colored images may be mapped onto the white light images of the wound.

The device maps biodistribution of bacteria within the wound site and on the surrounding skin and thus may aid in targeting specific tissue areas requiring swabbing or biopsy for microbiological testing. Furthermore, using the imaging device may permit the monitoring of the response of the bacterially-infected tissues to a variety of medical treatments, including the use of antibiotics and other therapies, such as photodynamic therapy (PDT), hyperbaric oxygen therapy (HOT), low level light therapy, or anti-Matrix Metalloproteinase (MMP). The device may be useful for visualization of bacterial biodistribution at the surface as well as within the tissue depth of the wound, and also for surrounding normal tissues. The device may thus be useful for indicating the spatial distribution of an infection.

In general, the device may be used to image and/or monitor targets such as a skin target, a tumor target, a wound target, a confined anatomical space or cavity, an oral target, an ear-nose-throat target, an ocular target, a genital target, an anal target, and any other suitable targets on a subject.

The image analysis algorithms may provide one or more of the following features:
Patient Digital Image Management
  Integration of a variety of image acquisition devices
  Records all imaging parameters including all exogenous fluorescence contrast agents
  Multiple scale and calibrations settings
  Built-in spectral image un-mixing and calculation algorithms for quantitative determination of tissue/bacterial autofluorescence and exogenous agent fluorescence signals
  Convenient annotation tools
  Digital archiving
  Web publishing
Basic Image Processing and Analysis
  Complete suite of image processing and quantitative analysis functions Image stitching algorithms will allow stitching of a series of panoramic or partially overlapping images of a wound into a single image, either in automated or manual mode.
  Easy to use measurement tools
  Intuitive set up of processing parameters
  Convenient manual editor
Report Generation
  Powerful image report generator with professional templates which may be integrated into existing clinical report infrastructures, or telemedicine/e-health patient medical data infrastructures. Reports may be exported to PDF, Word, Excel, for example.
Lame Library of Automated Solutions
  Customized automated solutions for various areas of wound assessment including quantitative image analysis.

Although image analysis algorithm, techniques, or software have been described, this description also extends to a computing device, a system, and a method for carrying out this image analysis.

Image-Guidance

The device may also be useful for providing fluorescent image-guidance, for example in surgical procedures, even without the use of dyes or markers. Certain tissues and/or organs may have different fluorescent spectra (e.g., endogenous fluorescence) when viewed using the imaging device, or example under certain excitation light conditions.

Application for Food Products

The imaging device may also be useful for monitoring food products (e.g., meat products) for contamination. This may be useful, for example, in food/animal product preparation in the meat, poultry, dairy, fish, and agricultural industries. The device may be used as part of an integrated multi-disciplinary approach to analytical laboratory services within this sector, which may provide capabilities including image-based detection of contamination and guidance for obtaining samples for testing. The device may be used for real-time detection, identification and monitoring of level of bacterial and other microbial meat contamination/adulteration of food products. It may be used for bacterial contamination tracking in the food processing plant environment, and thus may provide an image-based method for determining food safety and quality. In embodiments where the device is hand-held, compact and portable, the imaging device may be useful in food preparation areas to determine safety of food products from bacterial/microbial contamination. The device may also be used for relatively rapid detection and analysis of bacteria/microbes in meat samples (and on preparation surfaces) collected or sampled, for example as part of food-safety and quality regulated inspection process, during processing and in finished food products. This device may be used in the meat, horticulture and aquaculture industries in implementing food safety inspection/detection procedures that meet the requirements for food safety and quality. The device may be used to detect food contaminants, for example contaminants found in the meat, poultry, dairy and fish industries. This technology may be useful for as a fecal contaminant detection system, since fecal bacteria produce porphyrins which may be readily detected by the device.

Detection and accurate identification of foodborne pathogens, such as Listeria monocytogenes (LM), in food samples and processing lines may be critical both for ensuring food quality assurance and tracing of bacterial pathogen outbreaks within the food supply. Current detection methods employed in food production and processing facilities typically rely on multiple random surface sampling of equipment (e.g., swabbing), and subsequent molecular-based diagnostic assays (e.g., real-time polymerase chain reaction, RT-PCR) which may provide quantitative confirmation of the presence of LM, typically within 24-72 h. However, given time and cost restraints, typically only randomized selected zones of a given food production facility are tested for pathogen contamination at a time, and the significant potential of under-sampling during the "first pass" surface swabbing of equipment may result in undetected pathogens causing catastrophic health and economic consequences. In addition, the inability to i) rapidly sample all surface areas during the "first pass" swabbing to identify areas with high infection probability, ii) to visually document this initial screening process (e.g. no imaging methods available to date), iii) the delay in obtaining laboratory results, iv) the high-costs associated with current methods, and v) more importantly, the potential of missing deadly pathogen infections have prompted efforts to improve the early and accurate detection of food-borne pathogens cost-effectively.

The device may be useful in providing a relatively rapid and accurate way of detecting such pathogens. The device may be used with an assay of a multi-colored fluorescence probe 'cocktail' (e.g., a combination of two or more contrast agents) which may unequivocally identify (and may make visible) only viable Listeria monocytogenes from other Listeria species using highly-specific gene probe technology. This may allow specific detection of living LM in real-time, potentially minimizing the need for standard time-consuming enrichment methods. This method may also be expanded to include detection of other pathogens of interest, including *Enterobacter sakazakii, Camylobacter* species (*C. coli, C. jejuni* and *C. lari*), coliform bacteria and bacteria of the species *E. coli* (including lactose- and indol-negative *Escherichia coli*-strains), Salmonella, all bacteria belonging to the species *Staphylococcus aureus* and separately all bacteria belonging to the genus *Staphylococcus*, and *Pseudomonas aeruginosa*. Other bacteria may be detectable by selecting a suitable probe or combination of probes. For example a combination of two or more contrast agents may be designed to be specific to a certain bacteria and may result in a unique detectable fluorescent signature when imaged using the imaging device.

The imaging device may be used (e.g., when combined with applied exogenous bacteria-specific contrast agents, including a multi-targeted probe or a combination of probes) for relatively rapid "first pass" screening of food-preparation and handling surfaces for targeted swabbing and microbiological testing. This device may allow relatively rapid image-based surveillance of any surface of equipment and food products and may capture the fluorescence signature of food-borne bacteria/pathogens in real-time. The device may be used in combination with, for example, an assay of a multi-colored fluorescence probe 'cocktail' (and combinations thereof) which may unequivocally identify (and may make visible) only viable *Listeria monocytogenes* from other *Listeria* species using highly-specific gene probe technology, as described above. Such a probe 'cocktail' may be designed to specifically target certain pathogens based on a specific combination of probes known to be sensitive to such pathogens and known to give a signature fluorescence response. In addition to detection of such pathogens, the device may allow for the presence and/or location of different strains to be differentiated, based on their different signature fluorescence response.

Surface Contamination

The imaging device may be useful for detection of surface contamination, such as for detection of 'surface bacterial contamination' in health care settings. This device may be used for detecting and imaging of the presence of bacteria/microbes and other pathogens on a variety of surfaces/materials/instruments (in particular those related to surgery) in hospitals, chronic care facilities, and old age homes, where contamination is the leading source of infection. The device may be used in conjunction with standard detection, identification and enumeration of indicator organisms and pathogens strategies.

The systems and methods disclosed herein may form systems as outlined below and that are able to perform the processes outlined below:

A method |system| device for illuminating a subject with light of a calibrated intensity and for capturing closeup fluorescence digital images including:
an optical rangefinder
a digital camera sensor with optical fluorescence filter
one or more narrow wavelength band light emitters
a computing processor with memory
a user-display screen
a user input control
whereby:
the light emitters are turned on,
a preview camera image is presented to the user via the display screen,
the rangefinder value is presented to the user via the display screen
the user may activate the camera to capture an image
whereby the user may:
set the intensity of the light on the subject by adjusting the height of the device from the subject according to the rangefinder value on the screen and capture an image.

A method |system| device for capturing closeup digital images of a consistent magnification and perspective view including:
an optical rangefinder
one or more similar digital camera sensors
a computing processor with memory
a user-display screen
a user input control
whereby:
a preview camera image is presented to the user via the display screen,
the rangefinder value is presented to the user via the display screen
the user may activate one or another of the cameras to capture an image
whereby the user may:
set the view of the subject by adjusting the height of the device from the subject according to the rangefinder value on the screen and capture an image.

A method |system| device for capturing measurement-ready, closeup digital images of a subject including:
an optical rangefinder
a digital camera sensor
a computing processor with memory
a user-display screen
a user input control
image processing software
whereby:
the subject has 2 visible wound stickers attached,
a preview camera image is presented to the user via the display screen,
the rangefinder value is presented to the user via the display screen
the locations of the 2 stickers, if detected using image processing are continuously presented to the user via the display screen
the user may activate the camera to capture an image when stickers are detected.
whereby the user may:
set the view of the subject by adjusting the height of the device from the subject according to the rangefinder value on the screen,
set the view of the subject by adjusting the position of the device relative to the subject so that the stickers are detected and
capture an image.

It will be appreciated by those ordinarily skilled in the art having the benefit of this disclosure that the present disclosure provides various exemplary devices, systems, and methods for intraoperative and/or in vitro visualization of tumors and/or residual cancer cells on surgical margins. Further modifications and alternative embodiments of various aspects of the present disclosure will be apparent to those skilled in the art in view of this description.

Furthermore, the devices and methods may include additional components or steps that were omitted from the drawings for clarity of illustration and/or operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present disclosure may be utilized independently, all as would be apparent to one skilled in the art after having the benefit of the description herein. Changes may be made in the elements described herein without departing from the spirit and scope of the present disclosure and following claims, including their equivalents.

It is to be understood that the particular examples and embodiments set forth herein are non-limiting, and modifications to structure, dimensions, materials, and methodologies may be made without departing from the scope of the present disclosure.

Furthermore, this description's terminology is not intended to limit the present disclosure. For example, spatially relative terms—such as "beneath," "below," "lower," "above," "upper," "bottom," "right," "left," "proximal," "distal," "front," and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the drawings.

For the purposes of this specification and appended claims, unless otherwise indicated, all numbers expressing quantities, percentages or proportions, and other numerical values used in the specification and claims, are to be understood as being modified in all instances by the term "about" if they are not already. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

It should be understood that while the present disclosure has been described in detail with respect to various exemplary embodiments thereof, it should not be considered limited to such, as numerous modifications are possible without departing from the broad scope of the appended claims, including the equivalents they encompass.

We claim:

1. A portable, handheld imaging system, comprising:
   at least one excitation light source configured to emit excitation light during fluorescent imaging;
   a first image sensor configured to detect fluorescent wavelengths when the imaging system is in a fluorescent imaging mode;
   a first filter configured to permit passage of optical signals, responsive to illumination of a target surface with the excitation light and having a wavelength corresponding to one or more of bacterial fluorescence, bacterial autofluorescence, tissue fluorescence, and tissue autofluorescence the first filter being fixed to the first image sensor;
   a white light source configured to emit white light during white light imaging;
   a second image sensor configured to detect image data responsive to illumination of the target surface with the white light when the imaging system is in a white light imaging mode;
   a second filter configured to permit passage of optical signals, responsive to illumination of the target surface with the white light and having a wavelength in the visible light range, the second filter being fixed to the second image sensor;
   a third image sensor configured to detect image data responsive to illumination of the target surface with white light when the imaging system is in the white light imaging mode;
   a third filter configured to permit passage of optical signals, responsive to illumination of the target surface with the white light and having a wavelength in the visible light range, the third filter being fixed to the third image sensor; and
   a processor configured to receive the detected fluorescent and white light optical signals and to output a representation of the target surface to a display based on the detected optical signals.

2. The system of claim 1, wherein the at least one excitation light source is configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof.

3. The system of claim 1, wherein the at least one excitation light source is configured to emit excitation light having a wavelength of about 400 nm to about 450 nm.

4. The system of claim 1, wherein the at least one excitation light source is configured to emit excitation light having a wavelength of about 405 nm±10 nm.

5. The system of claim 1, wherein the at least one excitation light source is coupled to a housing of the portable, handheld imaging system.

6. The system of claim 1, wherein the first filter is further configured to block the passage of optical signals having a wavelength of 405 nm±10 nm.

7. The system of claim 1, wherein the first filter is configured to permit optical signals having a wavelength between about 500 nm and about 550 nm and/or optical signals having a wavelength between about 600 nm and about 660 nm to pass through the first filter to the first image sensor.

8. The system of claim 1, further comprising a housing having a display on a front side of the housing.

9. The system of claim 8, wherein the at least one excitation light source is positioned on a rear side of the housing.

10. The system of claim 1, wherein the at least one excitation light source includes first and second violet/blue LEDs, each LED configured to emit light having a wavelength of 405 nm±10 nm.

11. The system of claim 10, wherein the first and second violet/blue LEDs are positioned on opposite sides of a longitudinal axis of a housing, wherein the longitudinal axis passes through and top and bottom of the housing.

12. The system of claim 9, wherein the housing is a modular housing comprising a display unit and an optical unit.

13. The system of claim 12, wherein the optical unit is releasably attached to the display unit.

14. The system of claim 13, wherein the at least one excitation light source is contained in the optical unit.

15. The system of claim 14, wherein the white light source is contained in the optical unit.

16. The system of claim 15, wherein the display unit includes an interface configured to releasably receive an optical unit.

17. The system of claim 16, wherein the interface is defined, at least in part, by a heat sink of the system.

18. The system of claim 17, wherein the heat sink surrounds an opening configured to releasably receive the optical unit.

19. The system of claim 1, further comprising at least one of a thermal sensor configured to detect thermal information regarding the target surface, an ambient light sensor configured to indicate when ambient lighting conditions are sufficient to permit fluorescent imaging, or a range finder.

20. The system of claim 1, wherein the processor is further configured to receive image data from the second and third image sensors and output a stereoscopic or three-dimensional image.

21. The system of claim 1, further comprising a Wi-Fi and/or Bluetooth antenna.

22. The system of claim 1, wherein the processor is configured to wirelessly transmit and/or receive data.

23. The system of claim 1, further comprising a power source.

24. The system of claim 1, wherein the at least one excitation light source includes a first excitation light source and a second excitation light source.

25. The system of claim 24, wherein the first excitation light source is configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof.

26. The system of claim 25, wherein the first excitation light source is configured to emit excitation light having a wavelength of about 400 nm to about 450 nm.

27. The system of claim 26, wherein the first excitation light source is configured to emit excitation light having a wavelength of 405 nm±10 nm.

28. The system of claim 24, wherein the second excitation light source is configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof.

29. The system of claim 28, wherein the second excitation light source is configured to emit excitation light having a wavelength of about 750 nm-800 nm.

30. The system of claim 28, wherein the second excitation light source is configured to emit excitation light having a wavelength of about 760 nm±10 nm, about 770 nm±10 nm, or about 780 nm±10 nm.

31. The system of claim 1, wherein the first and second image sensors each comprise a complementary metal-oxide-semiconductor (CMOS) sensor.

32. The system of claim 1, further comprising an infrared radiation source.

33. The system of claim 32, wherein the system is configured to project infrared radiation onto the target surface and detect infrared radiation reflected from the target surface as well as any infrared fluorescence emitted by the target when excited by the appropriate excitation wavelength.

34. The system of claim 33, wherein the processor is further configured to generate a three-dimensional map of the target surface based on the detected reflected infrared radiation.

35. The system of claim 34, wherein the processor is further configured to generate a three-dimensional fluorescence image of the target surface based on the three-dimensional map, a two-dimensional white light image of the target surface, and a two-dimensional fluorescence image of the target surface.

36. A portable, modular handheld imaging system, comprising:
a first housing portion comprising:
at least one excitation light source configured to emit excitation light during fluorescent imaging,
a first image sensor configured to detect fluorescent wavelengths when the imaging system is in a fluorescent imaging mode,
a first filter configured to permit passage of optical signals, responsive to illumination of a target surface with the excitation light and having a wavelength corresponding to one or more of bacterial fluorescence, bacterial autofluorescence, tissue fluorescence, and tissue autofluorescence the first filter being fixed to the first image sensor,
a white light source configured to emit white light during white light imaging,
a second image sensor configured to detect image data responsive to illumination of the target surface with the white light when the imaging system is in a white light imaging mode,
a second filter configured to permit passage of optical signals, responsive to illumination of the target surface with the white light and having a wavelength in the visible light range, the second filter being fixed to the second image sensor,
a third image sensor configured to detect image data responsive to illumination of the target surface with white light when the imaging system is in a white light imaging mode, and
a third filter configured to permit passage of optical signals, responsive to illumination of the target surface with the white light and having a wavelength in the visible light range, the third filter being fixed to the third image sensor, and
a second housing portion configured to releasably receive the first housing portion and comprising:
a display, and
a processor configured to receive the detected fluorescent and white light optical signals and to output a representation of the target surface to the display based on the detected optical signals.

37. The system of claim 36, wherein the at least one excitation light source is configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof.

38. The system of claim 36, wherein the at least one excitation light source is configured to emit excitation light having a wavelength of about 400 nm to about 450 nm.

39. The system of claim 36, wherein the at least one excitation light source is configured to emit excitation light having a wavelength of about 405 nm±10 nm.

40. The system of claim 36, wherein the first filter is further configured to block the passage of optical signals having a wavelength of 405 nm±10 nm.

41. The system of claim 36, wherein the first filter is configured to permit optical signals having a wavelength between about 500 nm and about 550 nm and/or optical signals having a wavelength between about 600 nm and about 660 nm to pass through the first filter to the first image sensor.

42. The system of claim 36, wherein the at least one excitation light source includes first and second violet/blue LEDs, each LED configured to emit light having a wavelength of 405 nm±10 nm.

43. The system of claim 36, wherein the second housing portion further comprises a power source.

44. The system of claim 43, wherein the second housing further comprises an exterior surface with contacts for charging the power source.

45. The system of claim 36, wherein the first housing further comprises at least one of a thermal sensor configured to detect thermal information regarding the target surface, an ambient light sensor configured to indicate when ambient lighting conditions are sufficient to permit fluorescent imaging, or a range finder.

46. The system of claim 36, wherein the first housing further comprises a second excitation light source configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof.

47. The system of claim 46, wherein the second excitation light source is configured to emit excitation light having a wavelength of about 750 nm-800 nm.

48. The system of claim 47, wherein the second excitation light source is configured to emit excitation light having a wavelength of about 760 nm±10 nm, about 770 nm±10 nm, or about 780 nm±10 nm.

49. The system of claim 36, wherein the first housing further comprises a polarizing filter.

50. A portable, modular handheld imaging system kit, comprising:
a plurality of optical housing portions, each of the plurality of optical housing portions comprising:
at least one excitation light source configured to emit excitation light during fluorescent imaging,
a first image sensor configured to detect fluorescent wavelengths when the imaging system is in a fluorescent imaging mode,
a first filter configured to permit passage of optical signals, responsive to illumination of a target surface with the excitation light and having a wavelength corresponding to one or more of bacterial fluorescence, bacterial autofluorescence, tissue fluorescence, and tissue autofluorescence the first filter being fixed to the first image sensor,
a white light source configured to emit white light during white light imaging,
a second image sensor configured to detect image data responsive to illumination of the target surface with the white light when the imaging system is in a white light imaging mode;
a second filter configured to permit passage of optical signals, responsive to illumination of the target surface with the white light and having a wavelength in the visible light range, the second filter being fixed to the second image sensor,
a third image sensor configured to detect image data responsive to illumination of the target surface with white light when the imaging system is in a white light imaging mode, and
a third filter configured to permit passage of optical signals, responsive to illumination of the target surface with the white light and having a wavelength in the visible light range the third filter being fixed to the third image sensor; and
a base housing portion configured to releasably receive, interchangeably, each of the plurality of optical housing portions and comprising:
a display,
a power source configured to power the at least one excitation light source and the white light source, and
a processor configured to receive the detected fluorescent and white light optical signals and to output a representation of the target surface to the display based on the detected optical signals.

51. The kit of claim 50, wherein, in each of the plurality of optical housing portions, the at least one excitation light source is configured to emit excitation light having a wavelength of about 350 nm-about 400 nm, about 400 nm-about 450 nm, about 450 nm-about 500 nm, about 500 nm-about 550 nm, about 550 nm-about 600 nm, about 600 nm-about 650 nm, about 650 nm-about 700 nm, about 700 nm-about 750 nm, about 750 nm-about 800 nm, about 800 nm-about 850 nm, about 850 nm-about 900 nm, and/or combinations thereof.

52. The kit of claim 50, wherein the at least one excitation light source is configured to emit excitation light having a wavelength of about 400 nm to about 450 nm.

53. The kit of claim 50, wherein the at least one excitation light source is configured to emit excitation light having a wavelength of about 405 nm±10 nm.

54. The kit of claim 50, wherein the first filter is configured to permit optical signals having a wavelength between about 500 nm and about 550 nm and/or optical signals having a wavelength between about 600 nm and about 660 nm to pass through the first filter to the first image sensor.

55. The kit of claim 50, wherein the at least one excitation light source includes first and second violet/blue LEDs, each LED configured to emit light having a wavelength of 405 nm±10 nm.

56. The kit of claim 50, wherein a second one of the plurality of optical housing portions further includes a second excitation light source configured to emit excitation light having a wavelength different from a first excitation light source.

57. The kit of claim 56, wherein a second one of the plurality of optical housing portions is formed as an endoscopic housing portion.

58. The kit of claim 50, wherein one of the plurality of optical housing portions further comprises a range finder.

59. The kit of claim 50, wherein one of the plurality of optical housing portions further comprises a thermal sensor configured to detect thermal information regarding the target surface.

60. The kit of claim 50, wherein the base housing further comprises an ambient light sensor configured to indicate when ambient lighting conditions are sufficient to permit fluorescent imaging.

61. The kit of claim 50, wherein the base housing further comprises an exterior surface with contacts for charging the power source.

62. The kit of claim 50, wherein the base housing further comprises a heat sink.

63. The kit of claim 62, wherein the heat sink defines an opening in the base housing that is configured to releasably receive one of the plurality of optical housing portions.

64. The kit of claim 50, further comprising a darkening drape configured to be attached to a one of the plurality of optical housing portions.

65. The kit of claim 64, wherein the darkening drape is configured to reduce ambient light in a field of view of the first image sensor.

66. The kit of claim 64, wherein the darkening drape is one of a plurality of darkening drapes, each of the plurality of darkening drapes being configured to be attached to a respective one of the plurality of optical housing portions.

67. The kit of claim 57, further comprising a darkening drape configured to be attached to the endoscopic housing portion.

68. The kit of claim 67, wherein the darkening drape is configured to reduce ambient light in a field of view of the first image sensor.

69. The kit of claim 68, wherein the darkening drape is further configured to provide sterility in a surgical field and/or protect the optical housing portion from contaminants.

70. The kit of claim 50 wherein one of the plurality of optical housing portions further comprises a polarizing filter.

71. The kit of claim 50, wherein the base housing and one of the plurality of optical housing portions together form an imaging device and further comprising a sterile drape configured to create a sterile barrier between the imaging device and an environment in which the imaging device is used.

72. The kit of claim 50, further comprising one or more imaging agents or contrast agents.

73. A method of operating a modular, handheld fluorescence-based imaging device, comprising:
selecting an optical housing comprising optical components including at least one excitation light source for fluorescence imaging;
connecting the selected optical housing to a base body housing of the imaging device to provide power from a power source in the base body housing to the optical components in the optical housing;
illuminating a target with the at least one excitation light source to cause one or more of a part, a component, and a biomarker of the illuminated portion of the target to fluoresce, to reflect light, or to absorb light;
filtering a plurality of optical signals responsive to the illumination of the target with the excitation light, wherein filtering the plurality of optical signals includes preventing passage of reflected excitation light and permitting passage of optical signals having a wavelength corresponding to one or more of bacterial fluorescence, bacterial autofluorescence, tissue autofluorescence and exogenous tissue fluorescence through a set of at least three filters including a first fluorescent filter, a second white light filter, and a third white light filter, contained in the optical housing;
detecting the filtered optical signals with a set of at least three sensors including a first fluorescent sensor, a second white light sensor, and a third white light sensor, contained in the optical housing, wherein the first fluorescent filter is fixed to the first fluorescent sensor, the second white light filter is fixed to the second white light sensor, and the third white light filter is fixed to the third white light sensor; and
displaying the detected, filtered signals on at least one display of the base body housing as a composite image of the illuminated portion of the target, the composite image comprising fluorescent representations of various tissue components present in the illuminated portion of the target.

74. The method of claim 73, further comprising:
illuminating a target with a white light source contained in the optical housing;
filtering optical signals responsive to the illumination of the target with the white light with a visible light filter contained in the optical housing; and
detecting the filtered optical signals with an image sensor contained in the optical housing.

75. An imaging system kit, comprising:
the imaging system of claim 1; and
a sterile drape configured to create a sterile barrier between the imaging system and an environment the imaging system is used in.

76. The kit of claim 75, further comprising an imaging drape configured to reduce ambient light in an imaging environment of the imaging system.

77. The kit of claim 76, wherein the imaging drape includes a connector element configured to receive an optical housing of the imaging system.

78. The kit of claim 75, further comprising one or more imaging agents or contrast agents.

79. The system of claim 1, further comprising a third filter configured to detect and permit passage of optical signals, responsive to illumination of the target surface with the excitation light and having a wavelength corresponding to one or more of bacterial fluorescence, bacterial autofluorescence, tissue fluorescence, and tissue autofluorescence, to a third image sensor, wherein the wavelength of the third filter is different from the wavelength of the first filter and/or the second filter.

* * * * *